(12) United States Patent
Fung et al.

(10) Patent No.: US 10,654,805 B2
(45) Date of Patent: May 19, 2020

(54) PYRIDINETHIONES, PHARMACEUTICAL COMPOSITIONS THEREOF, AND THEIR THERAPEUTIC USE FOR TREATING A PROLIFERATIVE, INFLAMMATORY, NEURODEGENERATIVE, OR IMMUNE-MEDIATED DISEASE

(71) Applicant: BioTheryX, Inc., San Diego, CA (US)

(72) Inventors: Leah Fung, San Diego, CA (US); Robert Sullivan, Vista, CA (US); Kyle W. H. Chan, San Diego, CA (US); Frank Mercurio, Del Mar, CA (US); Armen Manoukian, North York (CA); Sam Scanga, Burlington (CA); Fabrizio Mastronardi, Maple (CA)

(73) Assignee: BioTheryX, Inc., San Diego, CA (US)

( * ) Notice: Subject to any disclaimer, the term of this patent is extended or adjusted under 35 U.S.C. 154(b) by 0 days.

(21) Appl. No.: 16/298,868

(22) Filed: Mar. 11, 2019

(65) Prior Publication Data
US 2019/0202788 A1    Jul. 4, 2019

Related U.S. Application Data

(62) Division of application No. 15/595,199, filed on May 15, 2017, now Pat. No. 10,233,153.

(60) Provisional application No. 62/337,256, filed on May 16, 2016.

(51) Int. Cl.
| | | |
|---|---|---|
| C07D 213/70 | (2006.01) |
| A61K 31/44 | (2006.01) |
| A61K 31/4418 | (2006.01) |
| A61K 45/06 | (2006.01) |

(52) U.S. Cl.
CPC ............ *C07D 213/70* (2013.01); *A61K 31/44* (2013.01); *A61K 31/4418* (2013.01); *A61K 45/06* (2013.01)

(58) Field of Classification Search
None
See application file for complete search history.

(56) References Cited

U.S. PATENT DOCUMENTS

| | | |
|---|---|---|
| 2,742,476 A | 4/1956 | Bernstein et al. |
| 3,850,883 A | 11/1974 | Masaki et al. |
| 4,009,168 A | 2/1977 | Masaki et al. |
| 4,080,329 A | 3/1978 | Muntwyler |
| 5,374,732 A | 12/1994 | Umenoto et al. |
| 6,664,280 B2 | 12/2003 | Lin et al. |
| 9,527,815 B2 | 12/2016 | Manoukian et al. |
| 2015/0368202 A1 | 12/2015 | Manoukian et al. |

FOREIGN PATENT DOCUMENTS

| | | |
|---|---|---|
| WO | 2007/124544 A1 | 11/2007 |

OTHER PUBLICATIONS

Praet et al, Neuroscience and Biobehavioral Reviews, vol. 47, pp. 485-505 (Year: 2014).*
Shikita et al, Journal of Radiation Research, 15 (2), pp. 116-118 (Year: 1974).*
Alonso et al., "Temporal trends in the incidence of multiple sclerosis: a systematic review," Neurology, 2008, 71, 129-135.
Ascherio et al., "Environmental risk factors for multiple sclerosis. Part I: the role of infection" Ann. Neural. 2007, 61, 288-299.
Ascherio et al., "Environmental risk factors for multiple sclerosi. Part II: Noninfectious factors," Ann. Neurol. 2007, 61, 504-513.
Compston et al., "Multiple sclerosis," Lancet 2008, 372, 1502-1517.
Debouverie, "Gender as a prognostic factor and its impact on the incidence of multiple sclerosis in Lorraine, France," J. Neurol. Sci. 2009, 286, 14-17.
Ebers, "Environmental factors and multiple sclerosis," Lancet Neurol. 2008, 7, 268-277.
Gawronski et al., "Treatment options for multiple sclerosis: current and emerging therapies," Pharmacotherapy 2010, 30, 916-927.
Krieger, "Multiple sclerosis therapeutic pipeline: opportunities and challenges," Mt. Sinai J. Med. 2011, 78, 192-206.
Luessi et al., "Neurodegeneration in multiple sclerosis: novel treatment strategies," Expert. Rev. Neurother. 2012, 12, 1061-1076.
Minagar, "Current and future therapies for multiple sclerosis," Scientifica 2013, Article ID 249101, 1-11.
Nakahara et al., "Current concepts in multiple sclerosis: autoimmunity versus oligodendrogliopathy," Clin. Rev. Allergy Immunol. 2012, 42, 26-34.
Noseworthy et al., "Multiple sclerosis," N. Engl. J. Med. 2000, 343, 938-952.
Orton et al., "Sex ratio of multiple sclerosis in Canada: a longitudinal study," Lancet Neurol. 2006, 5, 932-936.
Polshettiwar et al., J. Sulfur Chem. 2006, 27, 353-386.
Pugliatti et al., "The worldwide prevalence of multiple sclerosis," Clin Neurol. Neurosurg. 2002, 104, 182-191.

(Continued)

*Primary Examiner* — Zinna Northington Davis
(74) *Attorney, Agent, or Firm* — Jones Day

(57) ABSTRACT

Provided herein are pyridinethiones, for example, a compound of Formula I, and pharmaceutical compositions thereof. Also provided herein are methods of their use for treating, preventing, or ameliorating one or more symptoms of a proliferative, inflammatory, neurodegenerative, or immune-mediated disease (e.g., multiple sclerosis).

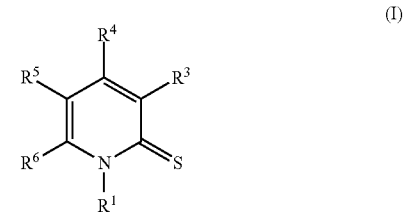

(I)

26 Claims, 3 Drawing Sheets

(56) References Cited

OTHER PUBLICATIONS

Ramagopalan et al., "Parent-of-origin effect in multiple sclerosis: observations from interracial matings," Neurology 2009, 73, 602-605.

Rodinovskaya et al., "One-pot synthesis of diverse 4-di(tri)fluoromethyl-3-cyanopyridine-2(1H)-thiones and their utilities in the cascade synthesis of annulated heterocycles," J. Comb. Chem. 2008, 10, 313-322.

Rodinovskaya et al., "Synthesis of annulated heterocyclic systems based on 4-CF3- or 4-CHF2-3-cyano-(1H)-pyridine-2-thiones," Russian Chem. Bull. 2013, 62, 2214-2226.

Zhao et al., "Synthesis and evaluation of pyrido-thieno-pyrimidines as potent and selective Cdc7 kinase inhibitors," Bioorg. Med. Chem. Lett. 2009, 19, 319-323.

Wang et al., "Discovery and structure-activity relationships study of novel thieno[2,3-b]pyridine analogues as hepatitis C virus inhibitors," Bioorg. Med. Chem. Lett. 2014, 24, 1581-1588.

Ghorbani-Choghamarani et al., "Cu(II)-Schiff base complex-functionalized magnetic Fe3O4 nanoparticles: a heterogeneous catalyst for various oxidation reactions," Appl. Organomet. Chem. 2015, 29, 170-175.

Liu et al., "Inhibition of Cancer-Associated Mutant Isocitrate Dehydrogenases: Synthesis, Structure-Activity Relationship, and Selective Antitumor Activity," J. Med. Chem. 2014, 57, 8307-8318.

CAS RN 149139-99-1 (1992).
CAS RN 300731-26-4 (Nov. 1, 2000).
CAS RN 368842-80-2 (Nov. 11, 2001).
CAS RN 1266125-63-6 (Mar. 3, 2011).
CAS RN 1595891-43-2 (May 2, 2014).
CAS RN 1806544-68-2 (Sep. 13, 2015).

Deeb et al., "Heterocyclic synthesis with 3-cyano-2(1H)pyridinethione: Synthesis of 3-oxo-2,3-dihydroisothiazolo [5,4-b]pyridine and related compounds," Monatshefte fur Chemie, 1990, 121, 281-287.

Krohnke, "The specific synthesis of pyridines and oligopyridines," Synthesis, 1976, 1-24.

Soto et al., "Preparation of pyridine-2(1H)-thiones from chalcones," Org. Prep. Proced. Int., 1984, 16, 11-24.

Wu et al., "Regulatory perspectives of Type II prodrug development and time-dependent toxicity management: nonclinical Pharm/Tox analysis and the role of comparative toxicology," Toxicology, 236:1-6 (2007).

* cited by examiner

PYRIDINETHIONES, PHARMACEUTICAL COMPOSITIONS THEREOF, AND THEIR THERAPEUTIC USE FOR TREATING A PROLIFERATIVE, INFLAMMATORY, NEURODEGENERATIVE, OR IMMUNE-MEDIATED DISEASE

CROSS REFERENCE TO RELATED APPLICATION

This application is a divisional application of U.S. application Ser. No. 15/595,199, filed May 15, 2017; which claims the benefit of U.S. Provisional Application No. 62/337,256, filed May 16, 2016; the disclosure of each of which is incorporated herein by reference in its entirety.

FIELD

Provided herein are pyridinethiones and pharmaceutical compositions thereof. Also provided herein are methods of their use for treating, preventing, or ameliorating one or more symptoms of a proliferative, inflammatory, neurodegenerative, or immune-mediated disease (e.g., multiple sclerosis).

BACKGROUND

Multiple sclerosis (MS), also known as disseminated sclerosis or encephalomyelitis disseminata, is a chronic, often disabling disease in which the insulating covers of nerve cells in the central nervous system (CNS) are damaged. Noseworthy et al., *N. Engl. J. Med.* 2000, 343, 938-952; Ebers, *Lancet Neurol.* 2008, 7, 268-277; Luessi et al., *Expert. Rev. Neurother.* 2012, 12, 1061-1076. This damage disrupts the ability of parts of the nervous system to communicate, resulting in a wide range of signs and symptoms, including physical, mental, and sometimes psychiatric problems. Compston et al., *Lancet* 2008, 372, 1502-1517. The most common clinical signs and symptoms of MS include sensory disturbance of the limbs (~30%), partial or complete visual loss (~15%), acute and subacute motor dysfunction of the limbs (~13%), diplopia (7%), and gait dysfunction (5%). Unfortunately, fifty percent of MS patients will need help to walk within 15 years after the onset of the disease. Noseworthy et al., *N. Engl. J. Med.* 2000, 343, 938-952.

The underlying mechanism of MS is thought to be either destruction by the immune system or failure of the myelin-producing cells. Nakahara et al., *Clin. Rev. Allergy Immunol.* 2012, 42, 26-34. Thus, MS is also considered as an immune-mediated disease. MS is thought to be triggered in genetically susceptible individuals by environmental factors such as infections. Ascherio et al., *Ann. Neurol.* 2007, 61, 288-299; Ascherio et al., *Ann. Neurol.* 2007, 61, 504-513; Compston et al., *Lancet* 2008, 372, 1502-1517.

The worldwide prevalence of MS is estimated at between 1.1 and 2.5 million cases of MS. Pugliatti et al., *Clin Neurol. Neurosurg.* 2002, 104, 182-191. Like many other immune-mediated diseases, MS is also more prevalent in women, especially those of childbearing age, than in men. Orton et al., *Lancet Neurol.* 2006, 5, 932-936; Alonso et al., *Neurology*, 2008, 71, 129-135; Debouverie, *J. Neurol. Sci.* 2009, 286, 14-17; Ramagopalan et al., *Neurology* 2009, 73, 602-605.

Four main clinical phenotypes of MS are recognized: relapsing-remitting MS (RR-MS); primary progressive MS (PP-MS); progressive relapsing MS (PR-MS); and secondary progressive MS (SP-MS). Minagar, *Scientifica* 2013, Article ID 249101, 1-11. RR-MS is the most prevalent form of the disease and also the type with the greatest gender imbalance, characterized by clearly defined attacks of worsening neurologic function, followed by partial or complete recovery periods (remissions). Id.

Current treatment strategies include modifying the disease course, treating exacerbations (also called attacks, relapses, or flare-ups), managing symptoms, improving function and safety, and providing emotional support. As of today, MS remains an incurable disease and thus, MS patients often require lifelong treatment. Gawronski et al., *Pharmacotherapy* 2010, 30, 916-927; Krieger, *Mt. Sinai J. Med.* 2011, 78, 192-206; Minagar, *Scientifica* 2013, Article ID 249101, 1-11. Therefore, there is a clear and unmet need to develop effective therapeutics for treating a proliferative, inflammatory, neurodegenerative, or immune-mediated disease, e.g., MS.

SUMMARY OF THE DISCLOSURE

Provided herein is a compound of Formula I:

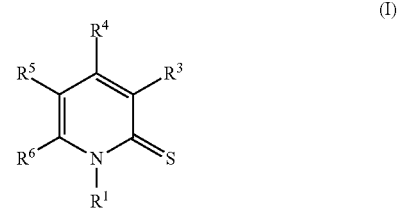

(I)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein:

$R^1$ is hydrogen or deuterium;

$R^3$ and $R^5$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)NR$^{1b}$R$^{1c}$, —C(O)S$R^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(=NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^4$ is (i) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (ii) —C(O)R$^{1a}$, —C(O)OR$^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, or —C(S)NR$^{1b}$R$^{1c}$;

$R^6$ is $C_{1-10}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^b R^c$, —C(O)S$R^a$, —C(N$R^a$)N$R^b R^c$, —C(S)$R^a$, —C(S)O$R^a$, —C(S)N$R^b R^c$, —O$R^a$, —OC(O)$R^a$, —OC(O)O$R^a$, —OC(O)N$R^b R^c$, —OC(O)S$R^a$, —OC(=N$R^a$)N$R^b R^c$, —OC(S)$R^a$, —OC(S)O$R^a$, —OC(S)N$R^b R^c$, —OS(O)$R^a$, —OS(O)$_2 R^a$, —OS(O)N$R^b R^c$, —OS(O)$_2$N$R^b R^c$, —N$R^b R^c$, —N$R^a$C(O)$R^d$, —N$R^a$C(O)O$R^d$, —N$R^a$C(O)N$R^b R^c$, —N$R^a$C(O)S$R^d$, —N$R^a$C(=N$R^d$)N$R^b R^c$, —N$R^a$C(S)$R^d$, —N$R^a$C(S)O$R^d$, —N$R^a$C(S)N$R^b R^c$, —N$R^a$S(O)$R^d$, —N$R^a$S(O)$_2 R^d$, —N$R^a$S(O)N$R^b R^c$, —N$R^a$S(O)$_2$N$R^b R^c$, —S$R^a$, —S(O)$R^a$, —S(O)$_2 R^a$, —S(O)N$R^b R^c$, and —S(O)$_2$N$R^b R^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from: (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^f R^g$, —C(O)S$R^e$, —C(N$R^e$)N$R^f R^g$, —C(S)$R^e$, —C(S)O$R^e$, —C(S)N$R^f R^g$, —O$R^e$, —OC(O)$R^e$, —OC(O)O$R^e$, —OC(O)N$R^f R^g$, —OC(O)S$R^e$, —OC(=N$R^e$)N$R^f R^g$, —OC(S)$R^e$, —OC(S)O$R^e$, —OC(S)N$R^f R^g$, —OS(O)$R^e$, —OS(O)$_2 R^e$, —OS(O)N$R^f R^g$, —OS(O)$_2$N$R^f R^g$, —N$R^f R^g$, —N$R^e$C(O)$R^h$, —N$R^e$C(O)O$R^f$, —N$R^e$C(O)N$R^f R^g$, —N$R^e$C(O)S$R^f$, —N$R^e$C(=N$R^h$)N$R^f R^g$, —N$R^e$C(S)$R^h$, —N$R^e$C(S)O$R^f$, —N$R^e$C(S)N$R^f R^g$, —N$R^e$S(O)$R^h$, —N$R^e$S(O)$_2 R^h$, —N$R^e$S(O)N$R^f R^g$, —N$R^e$S(O)$_2$N$R^f R^g$, —S$R^e$, —S(O)$R^e$, —S(O)$_2 R^e$, —S(O)N$R^f R^g$, and —S(O)$_2$N$R^f R^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In one embodiment, the compound of Formula I is not any one of 4,6-dimethylpyridine-2(1H)-thione, 6-methyl-4-trifluoromethylpyridine-2(1H)-thione, 4,6-di(trifluoromethyl)pyridine-2(1H)-thione, 6-isopropyl-4-trifluoromethylpyridine-2(1H)-thione, 6-butyl-4-trifluoromethylpyridine-2(1H)-thione, 6-isobutyl-4-trifluoromethylpyridine-2(1H)-thione, 6-cyclopropyl-4-(trifluoromethyl)-pyridine-2(1H)-thione, 6-cyclopropyl-4-(difluoromethyl)-2-thioxo-1,2-dihydropyridine-3-carbonitrile, and 6-cyclopropyl-4-(trifluoromethyl)-2-thioxo-1,2-dihydropyridine-3-carbonitrile.

Also provided herein is a pharmaceutical composition, comprising a compound of Formula I, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

Furthermore, provided herein is a method for treating one or more symptoms of a proliferative, inflammatory, neurodegenerative, or immune-mediated disease, in one embodiment, multiple sclerosis, in a subject, comprising administering to the subject a therapeutically effective amount of a compound of Formula I, or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

DETAILED DESCRIPTION

Figure 1:
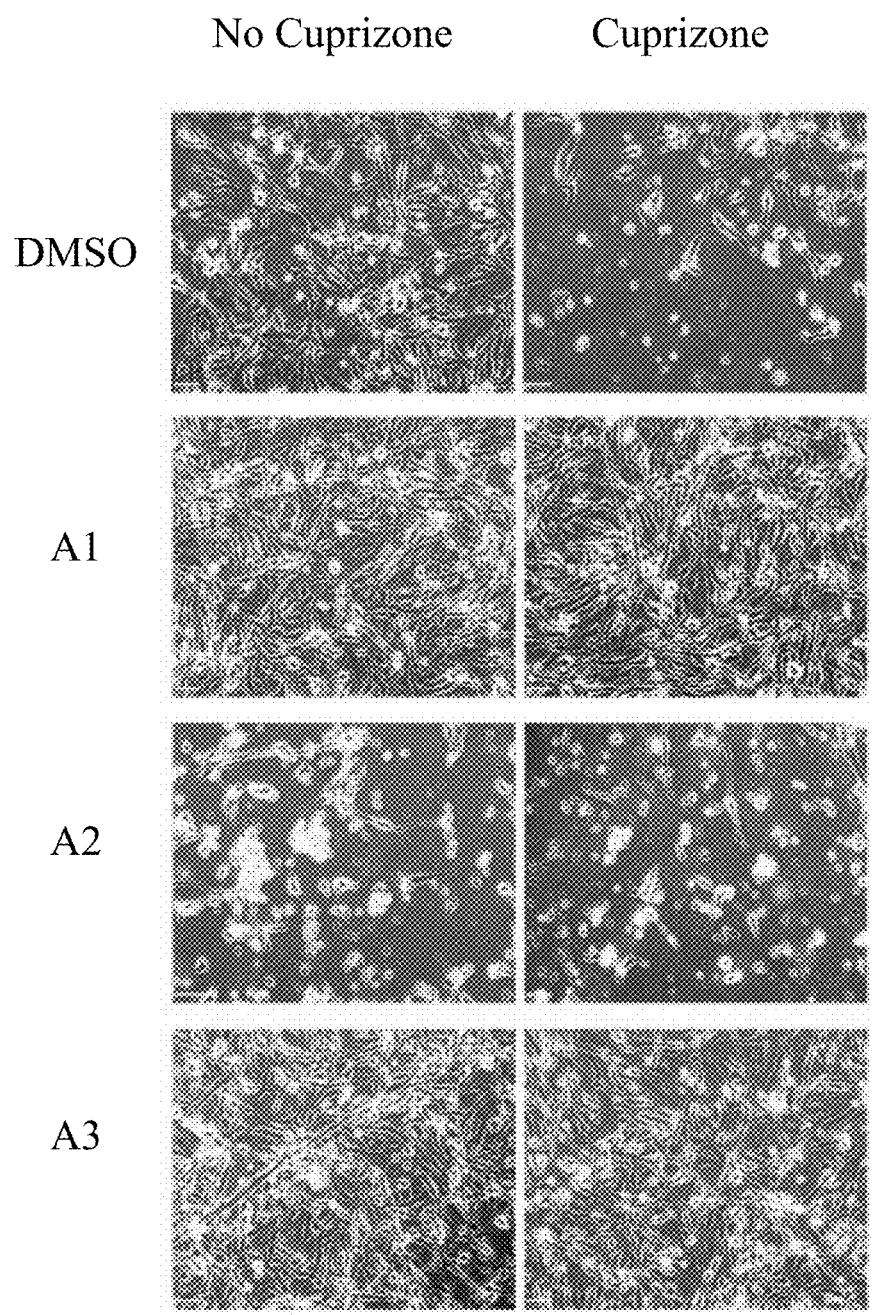
FIG. 1 shows the protection of human oligodendrocytes (MO3-13) with compounds A1 to A3 against cuprizone toxicity.

To facilitate understanding of the disclosure set forth herein, a number of terms are defined below.

Generally, the nomenclature used herein and the laboratory procedures in organic chemistry, medicinal chemistry, biochemistry, biology, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human or an animal) without excessive toxicity, irritation, allergic response, immunogenicity, or other problems or complications, commensurate with a reasonable benefit/risk ratio. See, *Remington: The Science and Practice of Pharmacy,* 22nd ed.; Allen Ed.: Philadelphia, Pa., 2012; *Handbook of Pharmaceutical Excipients,* 7th ed.; Rowe et al., Eds.; The Pharmaceutical Press and the American Pharmaceutical Association: 2012; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a disorder, disease, or condition. As used herein, "active ingredient" and "active substance" may be an optically active isomer of a compound described herein.

The terms "drug," "therapeutic agent," and "chemotherapeutic agent" refer to a compound or a pharmaceutical composition thereof, which is administered to a subject for treating, preventing, or ameliorating one or more symptoms of a disorder, disease, or condition.

The term "alkyl" refers to a linear or branched saturated monovalent hydrocarbon radical, wherein the alkyl is optionally substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

The term "alkenyl" refers to a linear or branched monovalent hydrocarbon radical, which contains one or more, in one embodiment, one, two, three, four, or five, in another embodiment, one, carbon-carbon double bond(s). The alkenyl is optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkynyl" refers to a linear or branched monovalent hydrocarbon radical, which contains one or more, in one embodiment, one, two, three, four, or five, in another embodiment, one, carbon-carbon triple bond(s). The alkynyl is optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 4 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 4 to 20 ($C_{4-20}$), 4 to 15 ($C_{4-15}$), 4 to 10 ($C_{4-10}$), or 4 to 6 ($C_{4-6}$) carbon atoms. Examples of alkynyl groups include, but are not limited to, ethynyl (—C≡CH), propynyl (including all isomeric forms, e.g., 1-propynyl (—C≡CCH$_3$) and propargyl (—CH$_2$C≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl).

The term "cycloalkyl" refers to a cyclic monovalent hydrocarbon radical, which is optionally substituted with one or more substituents Q as described herein. In one embodiment, the cycloalkyl is a saturated or unsaturated but non-aromatic, and/or bridged or non-bridged, and/or fused bicyclic group. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. In one embodiment, the cycloalkyl is monocyclic. In another embodiment, the cycloalkyl is bicyclic. In yet another embodiment, the cycloalkyl is polycyclic. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[2.1.1]hexyl, bicyclo[2.2.1]heptyl, decalinyl, and adamantyl.

The term "aryl" refers to a monovalent monocyclic aromatic hydrocarbon radical and/or monovalent polycyclic aromatic hydrocarbon radical that contain at least one aromatic carbon ring. In certain embodiments, the aryl has from 6 to 20 ($C_{6-20}$), from 6 to 15 ($C_{6-15}$), or from 6 to 10 ($C_{6-10}$) ring carbon atoms. Examples of aryl groups include, but are not limited to, phenyl, naphthyl, fluorenyl, azulenyl, anthryl, phenanthryl, pyrenyl, biphenyl, and terphenyl. The aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In one embodiment, the aryl is monocyclic. In another embodiment, the aryl is polycyclic. In yet another embodiment, the aryl is bicyclic. In still another embodiment, the aryl is tricyclic. In certain embodiments, the aryl is optionally substituted with one or more substituents Q as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl. In certain embodiments, the aralkyl is optionally substituted with one or more substituents Q as described herein.

The term "heteroaryl" refers to a monovalent monocyclic aromatic group or monovalent polycyclic aromatic group that contain at least one aromatic ring, wherein at least one aromatic ring contains one or more heteroatoms, each independently selected from O, S, and N, in the ring. The heteroaryl is bonded to the rest of a molecule through the aromatic ring. Each ring of a heteroaryl group can contain one or two O atoms, one or two S atoms, and/or one to four N atoms; provided that the total number of heteroatoms in each ring is four or less and each ring contains at least one carbon atom. In certain embodiments, the heteroaryl has from 5 to 20, from 5 to 15, or from 5 to 10 ring atoms. In one embodiment, the heteroaryl is monocyclic. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. In another embodiment, the heteroaryl is bicyclic. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. In yet another embodiment, the heteroaryl is tricyclic. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms, each independently selected from O, S, and N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. The heterocyclyl is bonded to the rest of a molecule through the non-aromatic ring. In certain embodiments, the heterocyclyl is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of heterocyclyls and heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl is optionally substituted with one or more substituents Q as described herein.

The term "halogen", "halide," or "halo" refers to fluorine, chlorine, bromine, and/or iodine.

The term "optionally substituted" is intended to mean that a group or substituent, such as an alkyl, alkenyl, alkynyl, cycloalkyl, aryl, aralkyl, heteroaryl, or heterocyclyl group, may be substituted with one or more, one, two, three, or four, substituents Q, each of which is independently selected from, e.g., (a) deuterium (-D), cyano (—CN), halo, and nitro (—$NO_2$); (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^b R^c$, —C(O)S$R^a$, —C(N$R^a$)N$R^b R^c$, —C(S)$R^a$, —C(S)O$R^a$, —C(S)N$R^b R^c$, —O$R^a$, —OC(O)$R^a$, —OC(O)O$R^a$, —OC(O)N$R^b R^c$, —OC(O)S$R^a$, —OC(=N$R^a$)N$R^b R^c$, —OC(S)$R^a$, —OC(S)O$R^a$, —OC(S)N$R^b R^c$, —OS(O)$R^a$, —OS(O)$_2 R^a$, —OS(O)N$R^b R^c$, —OS(O)$_2$N$R^b R^c$, —N$R^b R^c$, —N$R^a$C(O)$R^d$, —N$R^a$C(O)O$R^d$, —N$R^a$C(O)N$R^b R^c$, —N$R^a$C(O)S$R^d$, —N$R^a$C(=N$R^d$)N$R^b R^c$, —N$R^a$C(S)$R^d$, —N$R^a$C(S)O$R^d$, —N$R^a$C(S)N$R^b R^c$, —N$R^a$S(O)$R^d$, —N$R^a$S(O)$_2 R^d$, —N$R^a$S(O)N$R^b R^c$, —N$R^a$S(O)$_2$N$R^b R^c$, —S$R^a$, —S(O)$R^a$, —S(O)$_2 R^a$, —S(O)N$R^b R^c$, and —S(O)$_2$N$R^b R^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$. As used herein, all groups that can be substituted are "optionally substituted," unless otherwise specified.

In one embodiment, each $Q^a$ is independently selected from: (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^f R^g$, —C(O)S$R^e$, —C(N$R^e$)N$R^f R^g$, —C(S)$R^e$, —C(S)O$R^e$, —C(S)N$R^f R^g$, —O$R^e$, —OC(O)$R^e$, —OC(O)O$R^e$, —OC(O)N$R^f R^g$, —OC(O)S$R^e$, —OC(=N$R^e$)N$R^f R^g$, —OC(S)$R^e$, —OC(S)O$R^e$, —OC(S)N$R^f R^g$, —OS(O)$R^e$, —OS(O)$_2 R^e$, —OS(O)N$R^f R^g$, —OS(O)$_2$N$R^f R^g$, —N$R^f R^g$, —N$R^e$C(O)$R^h$, —N$R^e$C(O)O$R^f$, —N$R^e$C(O)N$R^f R^g$, —N$R^e$C(O)S$R^f$, —N$R^e$C(=N$R^h$)N$R^f R^g$, —N$R^e$C(S)$R^h$, —N$R^e$C(S)O$R^f$, —N$R^e$C(S)N$R^f R^g$, —N$R^e$S(O)$R^h$, —N$R^e$S(O)$_2 R^h$, —N$R^e$S(O)N$R^f R^g$, —N$R^e$S(O)$_2$N$R^f R^g$, —S$R^e$, —S(O)$R^e$, —S(O)$_2 R^e$, —S(O)N$R^f R^g$, and —S(O)$_2$N$R^f R^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, an optically active compound comprises about 95% or more of one enantiomer and about 5% or less of the other enantiomer based on the total weight of the enantiomeric mixture in question.

In describing an optically active compound, the prefixes R and S are used to denote the absolute configuration of the compound about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the compound, R and S.

The term "isotopically enriched" refers to a compound that contains an unnatural proportion of an isotope at one or more of the atoms that constitute such a compound. In certain embodiments, an isotopically enriched compound contains unnatural proportions of one or more isotopes, including, but not limited to, hydrogen ($^1H$), deuterium ($^2H$), tritium ($^3H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$), iodine-125 ($^{125}I$), iodine-127 ($^{127}I$), iodine-129 ($^{129}I$), and iodine-131 ($^{131}I$). In certain embodiments, an isotopically enriched compound is in a stable form, that is, non-radioactive. In certain embodiments, an isotopically enriched compound contains unnatural proportions of one or more isotopes, including, but not limited to, hydrogen ($^1H$), deuterium ($^2H$), carbon-12 ($^{12}C$), carbon-13 ($^{13}C$), nitrogen-14 ($^{14}N$), nitrogen-15 ($^{15}N$), oxygen-16 ($^{16}O$), oxygen-17 ($^{17}O$), oxygen-18 ($^{18}O$), fluorine-17 ($^{17}F$), phosphorus-31 ($^{31}P$), sulfur-32 ($^{32}S$), sulfur-33 ($^{33}S$), sulfur-34 ($^{34}S$), sulfur-36 ($^{36}S$), chlorine-35 ($^{35}Cl$), chlorine-37 ($^{37}Cl$), bromine-79 ($^{79}Br$), bromine-81 ($^{81}Br$), and iodine-127 ($^{127}I$). In certain embodiments, an isotopically enriched compound is in an unstable form, that is, radioactive. In certain embodiments, an isotopically enriched compound contains unnatural proportions of one or more isotopes, including, but not limited to, tritium ($^3H$), carbon-11 ($^{11}C$), carbon-14 ($^{14}C$), nitrogen-13 ($^{13}N$), oxygen-14 ($^{14}O$), oxygen-15 ($^{15}O$), fluorine-18 ($^{18}F$), phosphorus-32 ($^{32}P$), phosphorus-33 ($^{33}P$), sulfur-35 ($^{35}S$), chlorine-36 ($^{36}Cl$), iodine-123 ($^{123}I$), iodine-125 ($^{125}I$), iodine-129 ($^{129}I$), and iodine-131 ($^{131}I$). It will be understood that, in a compound as provided herein, any hydrogen can be $^2H$, as example, or any carbon can be $^{13}C$, as example, or any nitrogen can be $^{15}N$, as example, or any oxygen can be $^{18}O$, as example, where feasible according to the judgment of one of ordinary skill in the art.

The term "isotopic enrichment" refers to the percentage of incorporation of a less prevalent isotope (e.g., D for deuterium or hydrogen-2) of an element at a given position in a molecule in the place of a more prevalent isotope (e.g., $^1H$ for protium or hydrogen-1) of the element. As used herein, when an atom at a particular position in a molecule is designated as a particular less prevalent isotope, it is understood that the abundance of that isotope at that position is substantially greater than its natural abundance.

The term "isotopic enrichment factor" refers the ratio between the isotopic abundance in an isotopically enriched compound and the natural abundance of a specific isotope.

The term "hydrogen" or the symbol "H" refers to the composition of naturally occurring hydrogen isotopes, which include protium ($^1H$), deuterium ($^2H$ or D), and tritium ($^3H$), in their natural abundances. Protium is the most common hydrogen isotope having a natural abundance of more than 99.98%. Deuterium is a less prevalent hydrogen isotope having a natural abundance of about 0.0156%.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156% on average, deuterium enrichment at any position in a compound synthesized using non-enriched starting materials is about 0.0156% on average. As used herein, when a particular position in an isotopically enriched compound is designated as having deuterium, it is understood that the abundance of deuterium at that position in the compound is substantially greater than its natural abundance (0.0156%).

The term "carbon" or the symbol "C" refers to the composition of naturally occurring carbon isotopes, which include carbon-12 ($^{12}C$) and carbon-13 ($^{13}C$) in their natural abundances. Carbon-12 is the most common carbon isotope having a natural abundance of more than 98.89%. Carbon-13 is a less prevalent carbon isotope having a natural abundance of about 1.11%.

The term "carbon-13 enrichment" or "$^{13}C$ enrichment" refers to the percentage of incorporation of carbon-13 at a given position in a molecule in the place of carbon. For example, carbon-13 enrichment of 10% at a given position means that 10% of molecules in a given sample contain carbon-13 at the specified position. Because the naturally occurring distribution of carbon-13 is about 1.11% on average, carbon-13 enrichment at any position in a compound synthesized using non-enriched starting materials is about 1.11% on average. As used herein, when a particular position in an isotopically enriched compound is designated as having carbon-13, it is understood that the abundance of carbon-13 at that position in the compound is substantially greater than its natural abundance (1.11%).

The terms "substantially pure" and "substantially homogeneous" mean sufficiently homogeneous to appear free of readily detectable impurities as determined by standard analytical methods used by one of ordinary skill in the art, including, but not limited to, thin layer chromatography (TLC), gel electrophoresis, high performance liquid chromatography (HPLC), gas chromatography (GC), nuclear magnetic resonance (NMR), and mass spectrometry (MS);

or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 50%, at least about 70%, at least about 80%, at least about 90%, at least about 95%, at least about 98%, at least about 99%, or at least about 99.5% by weight of the molecules are a single compound, including a single enantiomer, a racemic mixture, or a mixture of enantiomers, as determined by standard analytical methods. As used herein, when an atom at a particular position in an isotopically enriched molecule is designated as a particular less prevalent isotope, a molecule that contains other than the designated isotope at the specified position is an impurity with respect to the isotopically enriched compound. Thus, for a deuterated compound that has an atom at a particular position designated as deuterium, a compound that contains a protium at the same position is an impurity.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof" has the same meaning as the phrase "(i) an enantiomer, a mixture of enantiomers, a mixture of two or more diastereomers, a tautomer, a mixture of two or more tautomers, or an isotopic variant of the compound referenced therein; or (ii) a pharmaceutically acceptable salt, solvate, hydrate, or prodrug of the compound referenced therein, or (iii) a pharmaceutically acceptable salt, solvate, hydrate, or prodrug of an enantiomer, a mixture of enantiomers, a mixture of two or more diastereomers, a tautomer, a mixture of two or more tautomers, or an isotopic variant of the compound referenced therein."

Compounds

In one embodiment, provided herein is a compound of Formula I:

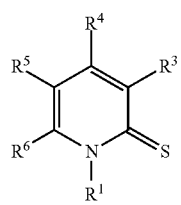

(I)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein:

$R^1$ is hydrogen or deuterium;

$R^3$ and $R^5$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(=NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{b}$R$^{c}$;

$R^4$ is (i) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (ii) —C(O)R$^{1a}$, —C(O)OR$^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, or —C(S)NR$^{1b}$R$^{1c}$;

$R^6$ is $C_{1-10}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)R$^a$, —C(O)OR$^a$, —C(O)NR$^b$R$^c$, —C(O)SR$^a$, —C(NR$^a$)NR$^b$R$^c$, —C(S)R$^a$, —C(S)OR$^a$, —C(S)NR$^b$R$^c$, —OR$^a$, —OC(O)R$^a$, —OC(O)OR$^a$, —OC(O)NR$^b$R$^c$, —OC(O)SR$^a$, —OC(=NR$^a$)NR$^b$R$^c$, —OC(S)R$^a$, —OC(S)OR$^a$, —OC(S)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(O)SR$^d$, —NR$^a$C(=NR$^d$)NR$^b$R$^c$, —NR$^a$C(S)R$^d$, —NR$^a$C(S)OR$^d$, —NR$^a$C(S)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from: (a) deuterium, cyano, halo, and nitro; (b) $C_{1-6}$ alkyl, $C_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(O)SR$^e$, —C(NR$^e$)NR$^f$R$^g$, —C(S)R$^e$, —C(S)OR$^e$, —C(S)NR$^f$R$^g$, —OR$^e$, —OC(O)R$^e$, —OC(O)OR$^e$, —OC(O)NR$^f$R$^g$, —OC(O)SR$^e$, —OC(=NR$^e$)NR$^f$R$^g$, —OC(S)R$^e$, —OC(S)OR$^e$, —OC(S)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(O)SR$^f$, —NR$^e$C(=NR$^h$)NR$^f$R$^g$, —NR$^e$C(S)R$^h$, —NR$^e$C(S)OR$^f$, —NR$^e$C(S)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

In another embodiment, provided herein is a compound of Formula I:

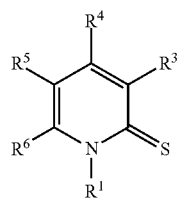

(I)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein:

R$^1$ is hydrogen or deuterium;

R$^3$ and R$^5$ are each independently (a) hydrogen, deuterium, cyano, halo, or nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(=NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^4$ is (i) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (ii) —C(O)R$^{1a}$, —C(O)OR$^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, or —C(S)NR$^{1b}$R$^{1c}$;

R$^6$ is C$_{3-10}$ cycloalkyl, C$_{6-14}$ aryl, C$_{7-15}$ aralkyl, heteroaryl, or heterocyclyl; and each R$^{1a}$, R$^{1b}$, R$^{1c}$, and R$^{1d}$ is independently hydrogen, deuterium, C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or R$^{1a}$ and R$^{1c}$ together with the C and N atoms to which they are attached form heterocyclyl; or R$^{1b}$ and R$^{1c}$ together with the N atom to which they are attached form heterocyclyl;

with the proviso that the compound is not any one of 6-cyclopropyl-4-(trifluoromethyl)-pyridine-2(1H)-thione, 6-cyclopropyl-4-(difluoromethyl)-2-thioxo-1,2-dihydropyridine-3-carbonitrile, and 6-cyclopropyl-4-(trifluoromethyl)-2-thioxo-1,2-dihydropyridine-3-carbonitrile;

wherein each alkyl, alkenyl, alkynyl, cycloalkyl, aryl, aralkyl, heteroaryl, and heterocyclyl is optionally substituted with one or more, in one embodiment, one, two, three, or four, substituents Q, where each Q is independently selected from (a) deuterium, cyano, halo, and nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl, each of which is further optionally substituted with one or more, in one embodiment, one, two, three, or four, substituents Q$^a$; and (c) —C(O)R$^a$, —C(O)OR$^a$, —C(O)NR$^b$R$^c$, —C(O)SR$^a$, —C(NR$^a$)NR$^b$R$^c$, —C(S)R$^a$, —C(S)OR$^a$, —C(S)NR$^b$R$^c$, —OR$^a$, —OC(O)R$^a$, —OC(O)OR$^a$, —OC(O)NR$^b$R$^c$, —OC(O)SR$^a$, —OC(=NR$^a$)NR$^b$R$^c$, —OC(S)R$^a$, —OC(S)OR$^a$, —OC(S)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(O)SR$^d$, —NR$^a$C(=NR$^d$)NR$^b$R$^c$, —NR$^a$C(S)R$^d$, —NR$^a$C(S)OR$^d$, —NR$^a$C(S)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl, each of which is optionally substituted with one or more, in one embodiment, one, two, three, or four, substituents Q$^a$; or (iii) R$^b$ and R$^c$ together with the N atom to which they are attached form heterocyclyl, optionally substituted with one or more, in one embodiment, one, two, three, or four, substituents Q$^a$;

wherein each Q$^a$ is independently selected from: (a) deuterium, cyano, halo, and nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(O)SR$^e$, —C(NR$^e$)NR$^f$R$^g$, —C(S)R$^e$, —C(S)OR$^e$, —C(S)NR$^f$R$^g$, —OR$^e$, —OC(O)R$^e$, —OC(O)OR$^e$, —OC(O)NR$^f$R$^g$, —OC(O)SR$^e$, —OC(=NR$^e$)NR$^f$R$^g$, —OC(S)R$^e$, —OC(S)OR$^e$, —OC(S)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(O)SR$^f$, —NR$^e$C(=NR$^h$)NR$^f$R$^g$, —NR$^e$C(S)R$^h$, —NR$^e$C(S)OR$^f$, —NR$^e$C(S)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

In yet another embodiment, provided herein is a compound of Formula I:

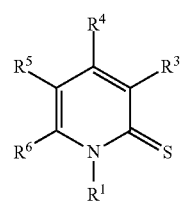

(I)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein:

$R^1$ is hydrogen or deuterium;

$R^3$ and $R^5$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(=N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(=N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^4$ is (i) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (ii) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, or —C(S)N$R^{1b}R^{1c}$;

$R^6$ is $C_{4-10}$ cycloalkyl, $C_{6-14}$ aryl, $C_{7-15}$ aralkyl, heteroaryl, or heterocyclyl; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(O)S$R^a$, —C(N$R^a$)N$R^bR^c$, —C(S)$R^a$, —C(S)O$R^a$, —C(S)N$R^bR^c$, —O$R^a$, —OC(O)$R^a$, —OC(O)O$R^a$, —OC(O)N$R^bR^c$, —OC(O)S$R^a$, —OC(=N$R^a$)N$R^bR^c$, —OC(S)$R^a$, —OC(S)O$R^a$, —OC(S)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(O)S$R^d$, —N$R^a$C(=N$R^d$)N$R^bR^c$, —N$R^a$C(S)$R^d$, —N$R^a$C(S)O$R^d$, —N$R^a$C(S)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from: (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(O)S$R^e$, —C(N$R^e$)N$R^fR^g$, —C(S)$R^e$, —C(S)O$R^e$, —C(S)N$R^fR^g$, —O$R^e$, —OC(O)$R^e$, —OC(O)O$R^e$, —OC(O)N$R^fR^g$, —OC(O)S$R^e$, —OC(=N$R^e$)N$R^fR^g$, —OC(S)$R^e$, —OC(S)O$R^e$, —OC(S)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^f$, —N$R^e$C(O)N$R^fR^g$, —N$R^e$C(O)S$R^f$, —N$R^e$(=N$R^h$)N$R^fR^g$, —N$R^e$C(S)$R^h$, —N$R^e$C(S)O$R^f$, —N$R^e$C(S)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and R together with the N atom to which they are attached form heterocyclyl.

In yet another embodiment, provided herein is a compound of Formula I:

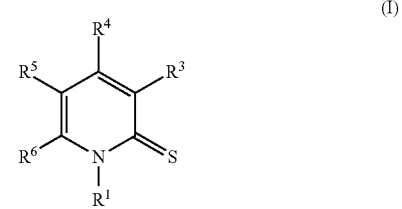

(I)

or an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof; wherein:

$R^1$ is hydrogen or deuterium;

$R^3$ and $R^5$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(=N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(=N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^4$ is (i) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (ii) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, or —C(S)N$R^{1b}R^{1c}$;

$R^6$ is $C_{1-10}$ alkyl, $C_{2-6}$ alkenyl, or $C_{2-6}$ alkynyl; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

with the proviso that the compound of Formula I is not any one of 4,6-dimethylpyridine-2(1H)-thione, 6-methyl-4-trifluoromethylpyridine-2(1H)-thione, 4,6-di(trifluoromethyl)pyridine-2(1H)-thione, 6-isopropyl-4-trifluoromethylpyridine-2(1H)-thione, 6-butyl-4-trifluoromethylpyridine-2(1H)-thione, and 6-isobutyl-4-trifluoromethylpyridine-2(1H)-thione;

wherein each alkyl, alkenyl, alkynyl, cycloalkyl, aryl, aralkyl, heteroaryl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(O)S$R^a$, —C(N$R^a$)N$R^bR^c$, —C(S)$R^a$, —C(S)O$R^a$, —C(S)N$R^bR^c$, —O$R^a$, —OC(O)$R^a$, —OC(O)O$R^a$, —OC(O)N$R^bR^c$, —OC(O)S$R^a$, —OC(=N$R^a$)N$R^bR^c$, —OC(S)$R^a$, —OC(S)O$R^a$, —OC(S)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(O)S$R^d$, —N$R^a$C(=N$R^d$)N$R^bR^c$, —N$R^a$C(S)$R^d$, —N$R^a$C(S)O$R^d$, —N$R^a$C(S)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from: (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(O)S$R^e$, —C(N$R^e$)N$R^fR^g$, —C(S)$R^e$, —C(S)O$R^e$, —C(S)N$R^fR^g$, —O$R^e$, —OC(O)$R^e$, —OC(O)O$R^e$, —OC(O)N$R^fR^g$, —OC(O)S$R^e$, —OC(=N$R^e$)N$R^fR^g$, —OC(S)$R^e$, —OC(S)O$R^e$, —OC(S)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^f$, —N$R^e$C(O)N$R^fR^g$, —N$R^e$C(O)S$R^f$, —N$R^e$(=N$R^h$)N$R^fR^g$, —N$R^e$C(S)$R^h$, —N$R^e$C(S)O$R^f$, —N$R^e$C(S)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In still another embodiment, provided herein is a compound of Formula I:

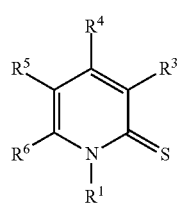

(I)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein:

$R^1$ is hydrogen or deuterium;

$R^3$ and $R^5$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(=N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(=N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^4$ is (i) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (ii) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, or —C(S)N$R^{1b}R^{1c}$;

$R^6$ is $C_{5-10}$ alkyl, $C_{2-6}$ alkenyl, or $C_{2-6}$ alkynyl; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(O)S$R^a$, —C(N$R^a$)N$R^bR^c$, —C(S)$R^a$, —C(S)O$R^a$, —C(S)N$R^bR^c$, —O$R^a$, —OC(O)$R^a$, —OC(O)O$R^a$, —OC(O)N$R^bR^c$, —OC(O)S$R^a$, —OC(=N$R^a$)N$R^bR^c$, —OC(S)$R^a$, —OC(S)O$R^a$, —OC(S)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(O)S$R^d$, —N$R^a$C(=N$R^d$)N$R^bR^c$, —N$R^a$C(S)$R^d$, —N$R^a$C(S)O$R^d$, —N$R^a$C(S)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from: (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(O)SR$^e$, —C(NR$^e$)NR$^f$R$^g$, —C(S)R$^e$, —C(S)OR$^e$, —C(S)NR$^f$R$^g$, —OR$^e$, —OC(O)R$^e$, —OC(O)OR$^e$, —OC(O)NR$^f$R$^g$, —OC(O)SR$^e$, —OC(=NR$^e$)NR$^f$R$^g$, —OC(S)R$^e$, —OC(S)OR$^e$, —OC(S)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(O)SR$^f$, —NR$^e$C(=NR$^h$)NR$^f$R$^g$, —NR$^e$C(S)R$^h$, —NR$^e$C(S)OR$^f$, —NR$^e$C(S)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^c$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

In one embodiment, the compound of Formula I is not any one of 4,6-dimethylpyridine-2(1H)-thione, 6-methyl-4-trifluoromethylpyridine-2(1H)-thione, 4,6-di(trifluoromethyl)pyridine-2(1H)-thione, 6-isopropyl-4-trifluoromethylpyridine-2(1H)-thione, 6-butyl-4-trifluoromethylpyridine-2(1H)-thione, and 6-isobutyl-4-trifluoromethylpyridine-2(1H)-thione. In another embodiment, the compound of Formula I is not 6-phenoxymethyl-4-methylpyridine-2(1H)-thione. In yet another embodiment, the compound of Formula I is not any one of 6-cyclopropyl-4-(trifluoromethyl)-pyridine-2(1H)-thione, 6-cyclopropyl-4-(difluoromethyl)-2-thioxo-1,2-dihydropyridine-3-carbonitrile, and 6-cyclopropyl-4-(trifluoromethyl)-2-thioxo-1,2-dihydropyridine-3-carbonitrile.

In one embodiment, at least one of R$^4$ and R$^6$ is not methyl.

In one embodiment, in Formula I,
R$^1$ is hydrogen or deuterium;
R$^3$ and R$^5$ are each independently (a) hydrogen, deuterium, cyano, halo, or nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl, each of which is optionally substituted with one or more substituents Q; or (c) —C(O)R$^{1a}$, —C(O)OR$^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(=NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$, where each R$^{1a}$, R$^{1b}$, R$^{1c}$, and R$^{1d}$ is as defined herein;
R$^4$ is C$_{1-6}$ alkyl, where the alkyl is optionally substituted with one or more substituents Q; and
R$^6$ is C$_{5-10}$ alkyl, C$_{2-6}$ alkenyl, C$_{2-6}$ alkynyl, C$_{4-10}$ cycloalkyl, C$_{6-14}$ aryl, C$_{7-15}$ aralkyl, heteroaryl, or heterocyclyl, each of which is optionally substituted with one or more substituents Q.

In another embodiment, in Formula I,
R$^1$ is hydrogen or deuterium;
R$^3$ and R$^5$ are each independently hydrogen or deuterium;
R$^4$ is C$_{1-6}$ alkyl, where the alkyl is optionally substituted with one or more substituents Q; and
R$^6$ is C$_{5-10}$ alkyl, C$_{2-6}$ alkenyl, C$_{2-6}$ alkynyl, C$_{4-10}$ cycloalkyl, C$_{6-14}$ aryl, C$_{7-15}$ aralkyl, heteroaryl, or heterocyclyl, each of which is optionally substituted with one or more substituents Q.

In yet another embodiment, in Formula I,
R$^1$ is hydrogen or deuterium;
R$^3$ and R$^5$ are each independently hydrogen or deuterium;
R$^4$ is C$_{1-6}$ alkyl, where the alkyl is optionally substituted with one or more substituents Q; and
R$^6$ is C$_{5-10}$ alkyl or C$_{4-10}$ cycloalkyl, each of which is optionally substituted with one or more substituents Q.

In yet another embodiment, in Formula I,
R$^1$ is hydrogen or deuterium;
R$^3$ and R$^5$ are each independently hydrogen or deuterium;
R$^4$ is C$_{1-6}$ alkyl, where the alkyl is optionally substituted with one or more substituents Q; and
R$^6$ is pentyl or cyclohexyl, each optionally substituted with one or more substituents Q.

In yet another embodiment, in Formula I,
R$^1$ is hydrogen or deuterium;
R$^3$ and R$^5$ are each independently hydrogen or deuterium;
R$^4$ is methyl or trifluoromethyl; and
R$^6$ is pentyl or cyclohexyl, each optionally substituted with one or more substituents Q.

In still another embodiment, in Formula I,
R$^1$ is hydrogen or deuterium;
R$^3$ and R$^5$ are each independently hydrogen or deuterium;
R$^4$ is methyl; and
R$^6$ is pentyl or cyclohexyl, each optionally substituted with one or more substituents Q.

In one embodiment, in Formula I,
R$^1$ is hydrogen or deuterium;
R$^3$ and R$^5$ are each independently (a) hydrogen, deuterium, cyano, halo, or nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl, each of which is optionally substituted with one or more substituents Q; or (c) —C(O)R$^{1a}$, —C(O)OR$^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(=NR$^{1d}$)NR$^{1b}$R$^{1c}$, —NR$^{1a}$C (S)$R^{1d}$, —$NR^{1a}C(S)OR^{1d}$, —$NR^{1a}C(S)NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$, where each $R^{1a}$, $R^{1b}$, $R^{1c}$, and $R^{1d}$ is as defined herein;

$R^4$ is $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; and $R^6$ is $C_{4-10}$ cycloalkyl, optionally substituted with one or more substituents Q.

In yet another embodiment, in Formula I,
$R^1$ is hydrogen or deuterium;
$R^3$ and $R^5$ are each independently hydrogen or deuterium;
$R^4$ is $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; and
$R^6$ is $C_{4-10}$ cycloalkyl, optionally substituted with one or more substituents Q.

In yet another embodiment, in Formula I,
$R^1$ is hydrogen or deuterium;
$R^3$ and $R^5$ are each independently hydrogen or deuterium;
$R^4$ is $C_{1-6}$ alkyl or $C_{6-14}$ aryl, each of which is optionally substituted with one or more substituents Q; and
$R^6$ is $C_{4-10}$ cycloalkyl, optionally substituted with one or more substituents Q.

In yet another embodiment, in Formula I,
$R^1$ is hydrogen or deuterium;
$R^3$ and $R^5$ are each independently hydrogen or deuterium;
$R^4$ is $C_{1-6}$ alkyl, optionally substituted with one or more substituents Q; and
$R^6$ is $C_{4-10}$ cycloalkyl, optionally substituted with one or more substituents Q.

In yet another embodiment, in Formula I,
$R^1$ is hydrogen or deuterium;
$R^3$ and $R^5$ are each independently hydrogen or deuterium;
$R^4$ is methyl or trifluoromethyl; and
$R^6$ is $C_{4-10}$ cycloalkyl, optionally substituted with one or more substituents Q.

In still another embodiment, in Formula I,
$R^1$ is hydrogen or deuterium;
$R^3$ and $R^5$ are each independently hydrogen or deuterium;
$R^4$ is methyl; and
$R^6$ is $C_{4-10}$ cycloalkyl, optionally substituted with one or more substituents Q.

In one embodiment, in Formula I,
$R^1$ is hydrogen or deuterium;
$R^3$ and $R^5$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (c) —$C(O)R^{1a}$, —$C(O)OR^{1a}$, —$C(O)NR^{1b}R^{1c}$, —$C(O)SR^{1a}$, —$C(NR^{1a})NR^{1b}R^{1c}$, —$C(S)R^{1a}$, —$C(S)OR^{1a}$, —$C(S)NR^{1b}R^{1c}$, —$OR^{1a}$, —$OC(O)R^{1a}$, —$OC(O)OR^{1a}$, —$OC(O)NR^{1b}R^{1c}$, —$OC(O)SR^{1a}$, —$OC(=NR^{1a})NR^{1b}R^{1c}$, —$OC(S)R^{1a}$, —$OC(S)OR^{1a}$, —$OC(S)NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(O)SR^{1d}$, —$NR^{1a}C(=NR^{1d})NR^{1b}R^{1c}$, —$NR^{1a}C(S)R^{1d}$, —$NR^{1a}C(S)OR^{1d}$, —$NR^{1a}C(S)NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$, where each $R^{1a}$, $R^{1b}$, $R^{1c}$, and $R^{1d}$ is as defined herein;

$R^4$ is $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; and $R^6$ is cyclohexyl, optionally substituted with one or more substituents Q.

In another embodiment, in Formula I,
$R^1$ is hydrogen or deuterium;
$R^3$ and $R^5$ are each independently hydrogen or deuterium;
$R^4$ is $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; and
$R^6$ is cyclohexyl, optionally substituted with one or more substituents Q.

In yet another embodiment, in Formula I,
$R^1$ is hydrogen or deuterium;
$R^3$ and $R^5$ are each independently hydrogen or deuterium;
$R^4$ is $C_{1-6}$ alkyl or $C_{6-14}$ aryl, each of which is optionally substituted with one or more substituents Q; and
$R^6$ is cyclohexyl, optionally substituted with one or more substituents Q.

In yet another embodiment, in Formula I,
$R^1$ is hydrogen or deuterium;
$R^3$ and $R^5$ are each independently hydrogen or deuterium;
$R^4$ is $C_{1-6}$ alkyl, optionally substituted with one or more substituents Q; and
$R^6$ is cyclohexyl, optionally substituted with one or more substituents Q.

In yet another embodiment, in Formula I,
$R^1$ is hydrogen or deuterium;
$R^3$ and $R^5$ are each independently hydrogen or deuterium;
$R^4$ is methyl or trifluoromethyl; and
$R^6$ is cyclohexyl, optionally substituted with one or more substituents Q.

In still another embodiment, in Formula I,
$R^1$ is hydrogen or deuterium;
$R^3$ and $R^5$ are each independently hydrogen or deuterium;
$R^4$ is methyl; and
$R^6$ is cyclohexyl, optionally substituted with one or more substituents Q.

In one embodiment, in Formula I,
$R^1$ is hydrogen or deuterium;
$R^3$ and $R^5$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (c) —$C(O)R^{1a}$, —$C(O)OR^{1a}$, —$C(O)NR^{1b}R^{1c}$, —$C(O)SR^{1a}$, —$C(NR^{1a})NR^{1b}R^{1c}$, —$C(S)R^{1a}$, —$C(S)OR^{1a}$, —$C(S)NR^{1b}R^{1c}$, —$OR^{1a}$, —$OC(O)R^{1a}$, —$OC(O)OR^{1a}$, —$OC(O)NR^{1b}R^{1c}$, —$OC(O)SR^{1a}$, —$OC(=NR^{1a})NR^{1b}R^{1c}$, —$OC(S)R^{1a}$, —$OC(S)OR^{1a}$, —$OC(S)NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(O)SR^{1d}$, —$NR^{1a}C(=NR^{1d})NR^{1b}R^{1c}$, —$NR^{1a}C(S)R^{1d}$, —$NR^{1a}C(S)OR^{1d}$, —$NR^{1a}C(S)NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^{1c}$, or —$S(O)_2NR^{1b}R^{1c}$, where each $R^{1a}$, $R^{1b}$, $R^{1c}$, and $R^{1d}$ is as defined herein;

$R^4$ is $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; and $R^6$ is $C_{5-10}$ alkyl, optionally substituted with one or more substituents Q.

In another embodiment, in Formula I,
$R^1$ is hydrogen or deuterium;
$R^3$ and $R^5$ are each independently hydrogen or deuterium;
$R^4$ is $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; and
$R^6$ is $C_{5-10}$ alkyl, optionally substituted with one or more substituents Q.

In yet another embodiment, in Formula I,
$R^1$ is hydrogen or deuterium;
$R^3$ and $R^5$ are each independently hydrogen or deuterium;
$R^4$ is $C_{1-6}$ alkyl or $C_{6-14}$ aryl, each of which is optionally substituted with one or more substituents Q; and
$R^6$ is $C_{5-10}$ alkyl, optionally substituted with one or more substituents Q.

In yet another embodiment, in Formula I,
$R^1$ is hydrogen or deuterium;
$R^3$ and $R^5$ are each independently hydrogen or deuterium;
$R^4$ is $C_{1-6}$ alkyl, optionally substituted with one or more substituents Q; and
$R^6$ is $C_{5-10}$ alkyl, optionally substituted with one or more substituents Q.

In yet another embodiment, in Formula I,
$R^1$ is hydrogen or deuterium;
$R^3$ and $R^5$ are each independently hydrogen or deuterium;
$R^4$ is methyl or trifluoromethyl; and
$R^6$ is $C_{5-10}$ alkyl, optionally substituted with one or more substituents Q.

In still another embodiment, in Formula I,
$R^1$ is hydrogen or deuterium;
$R^3$ and $R^5$ are each independently hydrogen or deuterium;
$R^4$ is methyl; and
$R^6$ is $C_{5-10}$ alkyl, optionally substituted with one or more substituents Q.

In one embodiment, in Formula I,
$R^1$ is hydrogen or deuterium;
$R^3$ and $R^5$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (c) —C(O)R$^{1a}$, —C(O)OR$^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(=NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$, where each R$^{1a}$, R$^{1b}$, R$^{1c}$, and R$^{1d}$ is as defined herein;
$R^4$ is $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; and
$R^6$ is pentyl, optionally substituted with one or more substituents Q.

In yet another embodiment, in Formula I,
$R^1$ is hydrogen or deuterium;
$R^3$ and $R^5$ are each independently hydrogen or deuterium;
$R^4$ is $C_{1-6}$ alkyl or $C_{6-14}$ aryl, each of which is optionally substituted with one or more substituents Q; and
$R^6$ is pentyl, optionally substituted with one or more substituents Q.

In yet another embodiment, in Formula I,
$R^1$ is hydrogen or deuterium;
$R^3$ and $R^5$ are each independently hydrogen or deuterium;
$R^4$ is $C_{1-6}$ alkyl, optionally substituted with one or more substituents Q; and
$R^6$ is pentyl, optionally substituted with one or more substituents Q.

In yet another embodiment, in Formula I,
$R^1$ is hydrogen or deuterium;
$R^3$ and $R^5$ are each independently hydrogen or deuterium;
$R^4$ is methyl or trifluoromethyl; and
$R^6$ is pentyl, optionally substituted with one or more substituents Q.

In still another embodiment, in Formula I,
$R^1$ is hydrogen or deuterium;
$R^3$ and $R^5$ are each independently hydrogen or deuterium;
$R^4$ is methyl; and
$R^6$ is pentyl, optionally substituted with one or more substituents Q.

In one embodiment, in Formula I,
$R^1$ is hydrogen or deuterium;
$R^3$ and $R^5$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (c) —C(O)R$^{1a}$, —C(O)OR$^{1a}$, —C(O)NR$^{1b}$R$^{1c}$, —C(O)SR$^{1a}$, —C(NR$^{1a}$)NR$^{1b}$R$^{1c}$, —C(S)R$^{1a}$, —C(S)OR$^{1a}$, —C(S)NR$^{1b}$R$^{1c}$, —OR$^{1a}$, —OC(O)R$^{1a}$, —OC(O)OR$^{1a}$, —OC(O)NR$^{1b}$R$^{1c}$, —OC(O)SR$^{1a}$, —OC(=NR$^{1a}$)NR$^{1b}$R$^{1c}$, —OC(S)R$^{1a}$, —OC(S)OR$^{1a}$, —OC(S)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(=NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$, where each R$^{1a}$, R$^{1b}$, R$^{1c}$, and R$^{1d}$ is as defined herein;
$R^4$ is $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; and
$R^6$ is trimethylpentyl, optionally substituted with one or more substituents Q.

In another embodiment, in Formula I,
$R^1$ is hydrogen or deuterium;
$R^3$ and $R^5$ are each independently hydrogen or deuterium;
$R^4$ is $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; and
$R^6$ is trimethylpentyl, optionally substituted with one or more substituents Q.

In yet another embodiment, in Formula I,
$R^1$ is hydrogen or deuterium;
$R^3$ and $R^5$ are each independently hydrogen or deuterium;
$R^4$ is $C_{1-6}$ alkyl or $C_{6-14}$ aryl, each of which is optionally substituted with one or more substituents Q; and
$R^6$ is trimethylpentyl, optionally substituted with one or more substituents Q.

In yet another embodiment, in Formula I,
$R^1$ is hydrogen or deuterium;
$R^3$ and $R^5$ are each independently hydrogen or deuterium;
$R^4$ is $C_{1-6}$ alkyl, optionally substituted with one or more substituents Q; and
$R^6$ is trimethylpentyl, optionally substituted with one or more substituents Q.

In yet another embodiment, in Formula I,
$R^1$ is hydrogen or deuterium;
$R^3$ and $R^5$ are each independently hydrogen or deuterium;
$R^4$ is methyl or trifluoromethyl; and
$R^6$ is trimethylpentyl, optionally substituted with one or more substituents Q.

In still another embodiment, in Formula I,
$R^1$ is hydrogen or deuterium;
$R^3$ and $R^5$ are each independently hydrogen or deuterium;
$R^4$ is methyl; and
$R^6$ is trimethylpentyl, optionally substituted with one or more substituents Q.

In one embodiment, in Formula I,
$R^1$ is hydrogen or deuterium;
$R^3$ and $R^5$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(=N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(=N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$, where each $R^{1a}$, $R^{1b}$, $R^{1c}$, and $R^{1d}$ is as defined herein;
$R^4$ is $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; and
$R^6$ is 2,4,4-trimethylpentyl.

In another embodiment, in Formula I,
$R^1$ is hydrogen or deuterium;
$R^3$ and $R^5$ are each independently hydrogen or deuterium;
$R^4$ is $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; and
$R^6$ is 2,4,4-trimethylpentyl.

In yet another embodiment, in Formula I,
$R^1$ is hydrogen or deuterium;
$R^3$ and $R^5$ are each independently hydrogen or deuterium;
$R^4$ is $C_{1-6}$ alkyl or $C_{6-14}$ aryl, each of which is optionally substituted with one or more substituents Q; and
$R^6$ is 2,4,4-trimethylpentyl.

In yet another embodiment, in Formula I,
$R^1$ is hydrogen or deuterium;
$R^3$ and $R^5$ are each independently hydrogen or deuterium;
$R^4$ is $C_{1-6}$ alkyl, optionally substituted with one or more substituents Q; and
$R^6$ is 2,4,4-trimethylpentyl.

In yet another embodiment, in Formula I,
$R^1$ is hydrogen or deuterium;
$R^3$ and $R^5$ are each independently hydrogen or deuterium;
$R^4$ is methyl or trifluoromethyl; and
$R^6$ is 2,4,4-trimethylpentyl.

In still another embodiment, in Formula I,
$R^1$ is hydrogen or deuterium;
$R^3$ and $R^5$ are each independently hydrogen or deuterium;
$R^4$ is methyl; and
$R^6$ is 2,4,4-trimethylpentyl.

In one embodiment, in Formula I,
$R^1$ is hydrogen or deuterium;
$R^3$ and $R^5$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(=N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(=N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$, where each $R^{1a}$, $R^{1b}$, $R^{1c}$, and $R^{1d}$ is as defined herein;
$R^4$ is $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; and
$R^6$ is $C_{1-6}$ alkyl or $C_{3-10}$ cycloalkyl, each of which optionally substituted with one or more substituents Q.

In another embodiment, in Formula I,
$R^1$ is hydrogen or deuterium;
$R^3$ and $R^5$ are each independently hydrogen or deuterium;
$R^4$ is $C_{1-6}$ alkyl, which is optionally substituted with one or more substituents Q; and
$R^6$ is $C_{1-6}$ alkyl or $C_{3-10}$ cycloalkyl, each of which optionally substituted with one or more substituents Q.

In yet another embodiment, in Formula I,
$R^1$ is hydrogen or deuterium;
$R^3$ and $R^5$ are each independently hydrogen or deuterium;
$R^4$ is $C_{1-6}$ alkyl, optionally substituted with one or more substituents Q; and
$R^6$ is methyl, propyl, cyclopropyl, cyclohexyl, or trimethylpentyl.

In yet another embodiment, in Formula I,
$R^1$ is hydrogen or deuterium;
$R^3$ and $R^5$ are each independently hydrogen or deuterium;
$R^4$ is methyl or propyl; and
$R^6$ is methyl, propyl, cyclopropyl, cyclohexyl, or trimethylpentyl.

In still another embodiment, in Formula I,
$R^1$ is hydrogen or deuterium;
$R^3$ and $R^5$ are each independently hydrogen or deuterium;
$R^4$ is methyl or isopropyl; and
$R^6$ is methyl, isopropyl, cyclopropyl, cyclohexyl, or 2,4,4-trimethylpentyl.

The groups, $R^1$, $R^3$, $R^4$, $R^5$, and $R^6$ in Formula I are further defined in the embodiments described herein. All combinations of the embodiments provided herein for such groups are within the scope of this disclosure.

In certain embodiments, $R^1$ is hydrogen. In certain embodiments, $R^1$ is deuterium.

In certain embodiments, $R^3$ is hydrogen. In certain embodiments, $R^3$ is deuterium. In certain embodiments, $R^3$ is cyano. In certain embodiments, $R^3$ is halo. In certain embodiments, $R^3$ is fluoro. In certain embodiments, $R^3$ is chloro. In certain embodiments, $R^3$ is nitro. In certain embodiments, $R^3$ is $C_{1-6}$ alkyl, optionally substituted with one or more substituents Q. In certain embodiments, $R^3$ is $C_{2-6}$ alkenyl, optionally substituted with one or more substituents Q. In certain embodiments, $R^3$ is $C_{2-6}$ alkynyl, optionally substituted with one or more substituents Q. In certain embodiments, $R^3$ is $C_{3-10}$ cycloalkyl, optionally substituted with one or more substituents Q. In certain embodiments, $R^3$ is $C_{6-14}$ aryl, optionally substituted with one or more substituents Q. In certain embodiments, $R^3$ is $C_{7-15}$ aralkyl, optionally substituted with one or more substituents Q. In certain embodiments, $R^3$ is heteroaryl, optionally substituted with one or more substituents Q. In certain embodiments, $R^3$ is heterocyclyl, optionally substituted with one or more substituents Q.

In certain embodiments, $R^3$ is —C(O)$R^{1a}$, wherein $R^{1a}$ is as defined herein. In certain embodiments, $R^3$ is —C(O)O$R^{1a}$, wherein $R^{1a}$ is as defined herein. In certain embodiments, $R^3$ is —C(O)N$R^{1b}R^{1c}$, wherein $R^{1b}$ and $R^{1c}$ are each as defined herein. In certain embodiments, $R^3$ is —C(O)S$R^{1a}$, wherein $R^{1a}$ is as defined herein. In certain embodiments, $R^3$ is —C(N$R^{1a}$)N$R^{1b}R^{1c}$, wherein $R^{1a}$, $R^{1b}$, and $R^{1c}$ are each as defined herein. In certain embodiments, $R^3$ is —C(S)$R^{1a}$, wherein $R^{1a}$ is as defined herein. In certain embodiments, $R^3$ is —C(S)O$R^{1a}$, wherein $R^{1a}$ is as defined herein. In certain embodiments, $R^3$ is —C(S)N$R^{1b}R^{1c}$, wherein $R^{1b}$ and $R^{1c}$ are each as defined herein. In certain embodiments, $R^3$ is —O$R^{1a}$, wherein $R^{1a}$ is as defined herein. In certain embodiments, $R^3$ is —OC(O)$R^{1a}$, wherein $R^{1a}$ is as defined herein. In certain embodiments, $R^3$ is —OC(O)O$R^{1a}$, wherein $R^{1a}$ is as defined herein. In certain embodiments, $R^3$ is —OC(O)N$R^{1b}R^{1c}$, wherein $R^{1b}$ and $R^{1c}$ are each as defined herein. In certain embodiments, $R^3$ is —OC(O)S$R^{1a}$, wherein $R^{1a}$ is as defined herein. In certain embodiments, $R^3$ is —OC(=N$R^{1a}$)N$R^{1b}R^{1c}$, wherein $R^{1a}$, $R^{1b}$, and $R^{1c}$ are each as defined herein. In certain embodiments, $R^3$ is —OC(S)$R^{1a}$, wherein $R^{1a}$ is as defined herein. In certain embodiments, $R^3$ is —OC(S)O$R^{1a}$, wherein $R^{1a}$ is as defined herein. In certain embodiments, $R^3$ is —OC(S)N$R^{1b}R^{1c}$, wherein $R^{1b}$ and $R^{1c}$ are each as defined herein. In certain embodiments, $R^3$ is —OS(O)$R^{1a}$, wherein $R^{1a}$ is as defined herein. In certain embodiments, $R^3$ is —OS(O)$_2R^{1a}$, wherein $R^{1a}$ is as defined herein. In certain embodiments, $R^3$ is —OS(O)N$R^{1b}R^{1c}$, wherein $R^{1b}$ and $R^{1c}$ are each as defined herein. In certain embodiments, $R^3$ is —OS(O)$_2$N$R^{1b}R^{1c}$, wherein $R^{1b}$ and $R^{1c}$ are each as defined herein. In certain embodiments, $R^3$ is —N$R^{1b}R^{1c}$, wherein $R^{1b}$ and $R^{1c}$ are each as defined herein. In certain embodiments, $R^3$ is —N$R^{1a}$C(O)$R^{1d}$, wherein $R^{1a}$ and $R^{1d}$ are each as defined herein. In certain embodiments, $R^3$ is —N$R^{1a}$C(O)O$R^{1d}$, wherein $R^{1a}$ and $R^{1d}$ are each as defined herein. In certain embodiments, $R^3$ is —N$R^{1a}$C(O)N$R^{1b}R^{1c}$, wherein $R^{1a}$, $R^{1b}$, and $R^{1c}$ are each as defined herein. In certain embodiments, $R^3$ is —N$R^{1a}$C(O)S$R^{1d}$, wherein $R^{1a}$ and $R^{1d}$ are each as defined herein. In certain embodiments, $R^3$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^3$ is —N$R^{1a}$C(S)$R^{1d}$, wherein $R^{1a}$ and $R^{1d}$ are each as defined herein. In certain embodiments, $R^3$ is —N$R^{1a}$C(S)O$R^{1d}$, wherein $R^{1a}$ and $R^{1d}$ are each as defined herein. In certain embodiments, $R^3$ is —N$R^{1a}$C(S)N$R^{1b}R^{1c}$, wherein $R^{1a}$, $R^{1b}$, and $R^{1c}$ are each as defined herein. In certain embodiments, $R^3$ is —N$R^{1a}$S(O)$R^{1d}$, wherein $R^{1a}$ and $R^{1d}$ are each as defined herein. In certain embodiments, $R^3$ is —N$R^{1a}$S(O)$_2R^{1d}$, wherein $R^{1a}$ and $R^{1d}$ are each as defined herein. In certain embodiments, $R^3$ is —N$R^{1a}$S(O)N$R^{1b}R^{1c}$, wherein $R^{1a}$, $R^{1b}$, and $R^{1c}$ are each as defined herein. In certain embodiments, $R^3$ is —N$R^{1a}$S(O)$_2$N$R^{1b}R^{1c}$, wherein $R^{1a}$, $R^{1b}$, and $R^{1c}$ are each as defined herein. In certain embodiments, $R^3$ is —S$R^{1a}$, wherein $R^{1a}$ is as defined herein. In certain embodiments, $R^3$ is —S(O)$R^{1a}$, wherein $R^{1a}$ is as defined herein. In certain embodiments, $R^3$ is —S(O)$_2R^{1a}$, wherein $R^{1a}$ is as defined herein. In certain embodiments, $R^3$ is —S(O)N$R^{1b}R^{1c}$, wherein $R^{1b}$ and $R^{1c}$ are each as defined herein. In certain embodiments, $R^3$ is —S(O)$_2$N$R^{1b}R^{1c}$, wherein $R^{1b}$ and $R^{1c}$ are each as defined herein.

In certain embodiments, $R^4$ is $C_{1-6}$ alkyl, optionally substituted with one or more substituents Q. In certain embodiments, $R^4$ is methyl, optionally substituted with one or more substituents Q. In certain embodiments, $R^4$ is methyl. In certain embodiments, $R^4$ is methyl or propyl. In certain embodiments, $R^4$ is methyl or isopropyl. In certain embodiments, $R^4$ is methyl, optionally substituted with one, two, or three deuterium, fluoro, or hydroxyl. In certain embodiments, $R^4$ is —CH$_2$D, —CHD$_2$, or —CD$_3$. In certain embodiments, $R^4$ is —CH$_2$F (fluoromethyl or monofluoromethyl), —CHF$_2$ (difluoromethyl), or —CF$_3$ (trifluoromethyl). In certain embodiments, $R^4$ is —CH$_2$OH, —CH(OH)$_2$ (i.e., CHO), or —C(OH)$_3$ (i.e., COOH). In certain embodiments, $R^4$ is $C_{2-6}$ alkyl, optionally substituted with one or more substituents Q. In certain embodiments, $R^4$ is $C_{2-6}$ alkenyl, optionally substituted with one or more substituents Q. In certain embodiments, $R^4$ is $C_{2-6}$ alkynyl, optionally substituted with one or more substituents Q. In certain embodiments, $R^4$ is $C_{3-10}$ cycloalkyl, optionally substituted with one or more substituents Q. In certain embodiments, $R^4$ is $C_{6-14}$ aryl, optionally substituted with one or more substituents Q. In certain embodiments, $R^4$ is monocyclic $C_{6-14}$ aryl, optionally substituted with one or more substituents Q. In certain embodiments, $R^4$ is phenyl, optionally substituted with one or more substituents Q. In certain embodiments, $R^4$ is phenyl. In certain embodiments, $R^4$ is $C_{7-15}$ aralkyl, optionally substituted with one or more substituents Q. In certain embodiments, $R^4$ is heteroaryl, optionally substituted with one or more substituents Q. In certain embodiments, $R^4$ is heterocyclyl, optionally substituted with one or more substituents Q.

In certain embodiments, $R^4$ is —C(O)$R^{1a}$, wherein $R^{1a}$ is as defined herein. In certain embodiments, $R^4$ is —C(O)O$R^{1a}$, wherein $R^{1a}$ is as defined herein. In certain embodiments, $R^4$ is —C(O)N$R^{1b}R^{1c}$, wherein $R^{1b}$ and $R^{1c}$ are each as defined herein. In certain embodiments, $R^4$ is —C(O)NH$R^{1c}$, wherein $R^{1c}$ is as defined herein. In certain embodiments, $R^4$ is —C(O)NH-butyl. In certain embodiments, $R^4$ is —C(O)S$R^{1a}$, wherein $R^{1a}$ is as defined herein. In certain embodiments, $R^4$ is —C(N$R^{1a}$)N$R^{1b}R^{1c}$, wherein $R^{1a}$, $R^{1b}$, and $R^{1c}$ are each as defined herein. In certain embodiments, $R^4$ is —C(S)$R^{1a}$, wherein $R^{1a}$ is as defined herein. In certain embodiments, $R^4$ is —C(S)O$R^{1a}$, wherein $R^{1a}$ is as defined herein. In certain embodiments, $R^4$ is —C(S)N$R^{1b}R^{1c}$, wherein $R^{1b}$ and $R^{1c}$ are each as defined herein.

In certain embodiments, $R^5$ is hydrogen. In certain embodiments, $R^5$ is deuterium. In certain embodiments, $R^5$ is cyano. In certain embodiments, $R^5$ is halo. In certain embodiments, $R^5$ is fluoro. In certain embodiments, $R^5$ is chloro. In certain embodiments, $R^5$ is nitro. In certain embodiments, $R^5$ is $C_{1-6}$ alkyl, optionally substituted with one or more substituents Q. In certain embodiments, $R^5$ is $C_{2-6}$ alkenyl, optionally substituted with one or more substituents Q. In certain embodiments, $R^5$ is $C_{2-6}$ alkynyl, optionally substituted with one or more substituents Q. In certain embodiments, $R^5$ is $C_{3-10}$ cycloalkyl, optionally substituted with one or more substituents Q. In certain embodiments, $R^5$ is $C_{6-14}$ aryl, optionally substituted with one or more substituents Q. In certain embodiments, $R^5$ is $C_{7-15}$ aralkyl, optionally substituted with one or more substituents Q. In certain embodiments, $R^5$ is heteroaryl, optionally substituted with one or more substituents Q. In certain embodiments, $R^5$ is heterocyclyl, optionally substituted with one or more substituents Q.

In certain embodiments, $R^5$ is —C(O)$R^{1a}$, wherein $R^{1a}$ is as defined herein. In certain embodiments, $R^5$ is —C(O)O$R^{1a}$, wherein $R^{1a}$ is as defined herein. In certain embodiments, $R^5$ is —C(O)N$R^{1b}R^{1c}$, wherein $R^{1b}$ and $R^{1c}$ are each as defined herein. In certain embodiments, $R^5$ is —C(O)S$R^{1a}$, wherein $R^{1a}$ is as defined herein. In certain embodiments, $R^5$ is —C(N$R^{1a}$)N$R^{1b}R^{1c}$, wherein $R^{1a}$, $R^{1b}$, and $R^{1c}$ are each as defined herein. In certain embodiments, $R^5$ is —C(S)$R^{1a}$, wherein $R^{1a}$ is as defined herein. In certain embodiments, $R^5$ is —C(S)O$R^{1a}$, wherein $R^{1a}$ is as defined herein. In certain embodiments, $R^5$ is —C(S)N$R^{1b}R^{1c}$, wherein $R^{1b}$ and $R^{1c}$ are each as defined herein. In certain embodiments, $R^5$ is —O$R^{1a}$, wherein $R^{1a}$ is as defined herein. In certain embodiments, $R^5$ is —OC(O)$R^{1a}$, wherein $R^{1a}$ is as defined herein. In certain embodiments, $R^5$ is —OC(O)O$R^{1a}$, wherein $R^{1a}$ is as defined herein. In certain embodiments, $R^5$ is —OC(O)N$R^{1b}R^{1c}$, wherein $R^{1b}$ and $R^{1c}$ are each as defined herein. In certain embodiments, $R^5$ is —OC(O)S$R^{1a}$, wherein $R^{1a}$ is as defined herein. In certain embodiments, $R^5$ is —OC(=N$R^{1a}$)N$R^{1b}R^{1c}$, wherein $R^{1a}$, $R^{1b}$, and $R^{1c}$ are each as defined herein. In certain embodiments, $R^5$ is —OC(S)$R^{1a}$, wherein $R^{1a}$ is as defined herein. In certain embodiments, $R^5$ is —OC(S)O$R^{1a}$, wherein $R^{1a}$ is as defined herein. In certain embodiments, $R^5$ is —OC(S)N$R^{1b}R^{1c}$, wherein $R^{1b}$ and $R^{1c}$ are each as defined herein. In certain embodiments, $R^5$ is —OS(O)$R^{1a}$, wherein $R^{1a}$ is as defined herein. In certain embodiments, $R^5$ is —OS(O)$_2R^{1a}$, wherein $R^{1a}$ is as defined herein. In certain embodiments, $R^5$ is —OS(O)N$R^{1b}R^{1c}$, wherein $R^{1b}$ and $R^{1c}$ are each as defined herein. In certain embodiments, $R^5$ is —OS(O)$_2$N$R^{1b}R^{1c}$, wherein $R^{1b}$ and $R^{1c}$ are each as defined herein. In certain embodiments, $R^5$ is —N$R^{1b}R^{1c}$, wherein $R^{1b}$ and $R^{1c}$ are each as defined herein. In certain embodiments, $R^5$ is —N$R^{1a}$C(O)$R^{1d}$, wherein $R^{1a}$ and $R^{1d}$ are each as defined herein. In certain embodiments, $R^5$ is —N$R^{1a}$C(O)O$R^{1d}$, wherein $R^{1a}$ and $R^{1d}$ are each as defined herein. In certain embodiments, $R^5$ is —N$R^{1a}$C(O)N$R^{1b}R^{1c}$, wherein $R^{1a}$, $R^{1b}$, and $R^{1c}$ are each as defined herein. In certain embodiments, $R^5$ is —N$R^{1a}$C(O)S$R^{1d}$, wherein $R^{1a}$ and $R^{1d}$ are each as defined herein. In certain embodiments, $R^5$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^5$ is —N$R^{1a}$C(S)$R^{1d}$, wherein $R^{1a}$ and $R^{1d}$ are each as defined herein. In certain embodiments, $R^5$ is —N$R^{1a}$C(S)O$R^{1d}$, wherein $R^{1a}$ and $R^{1d}$ are each as defined herein. In certain embodiments, $R^5$ is —N$R^{1a}$C(S)N$R^{1b}R^{1c}$, wherein $R^{1a}$, $R^{1b}$, and $R^{1c}$ are each as defined herein. In certain embodiments, $R^5$ is —N$R^{1a}$S(O)$R^{1d}$, wherein $R^{1a}$ and $R^{1d}$ are each as defined herein. In certain embodiments, $R^5$ is —N$R^{1a}$S(O)$_2R^{1d}$, wherein $R^{1a}$ and $R^{1d}$ are each as defined herein. In certain embodiments, $R^5$ is —N$R^{1a}$S(O)N$R^{1b}R^{1c}$, wherein $R^{1a}$, $R^{1b}$, and $R^{1c}$ are each as defined herein. In certain embodiments, $R^5$ is —N$R^{1a}$S(O)$_2$N$R^{1b}R^{1c}$, wherein $R^{1a}$, $R^{1b}$, and $R^{1c}$ are each as defined herein. In certain embodiments, $R^5$ is —S$R^{1a}$, wherein $R^{1a}$ is as defined herein. In certain embodiments, $R^5$ is —S(O)$R^{1a}$, wherein $R^{1a}$ is as defined herein. In certain embodiments, $R^5$ is —S(O)$_2R^{1a}$, wherein $R^{1a}$ is as defined herein. In certain embodiments, $R^5$ is —S(O)N$R^{1b}R^{1c}$, wherein $R^{1b}$ and $R^{1c}$ are each as defined herein. In certain embodiments, $R^5$ is —S(O)$_2$N$R^{1b}R^{1c}$, wherein $R^{1b}$ and $R^{1c}$ are each as defined herein.

In certain embodiments, $R^3$ and $R^5$ are hydrogen.

In certain embodiments, $R^6$ is $C_{1-10}$ alkyl, optionally substituted with one or more substituents Q. In certain embodiments, $R^6$ is $C_{2-10}$ alkyl, optionally substituted with one or more substituents Q. In certain embodiments, $R^6$ is pentyl, optionally substituted with one or more substituents Q. In certain embodiments, $R^6$ is pentyl, optionally substituted with one or more substituents Q. In certain embodiments, $R^6$ is trimethylpentyl, optionally substituted with one or more substituents Q. In certain embodiments, $R^6$ is 2,4,4-trimethylpentyl. In certain embodiments, $R^6$ is methyl or propyl. In certain embodiments, $R^6$ is methyl or isopropyl. In certain embodiments, $R^6$ is $C_{2-6}$ alkynyl, optionally substituted with one or more substituents Q. In certain embodiments, $R^6$ is $C_{3-10}$ cycloalkyl, optionally substituted with one or more substituents Q. In certain embodiments, $R^6$ is $C_{4-10}$ cycloalkyl, optionally substituted with one or more substituents Q. In certain embodiments, $R^6$ is monocyclic $C_{3-10}$ cycloalkyl, optionally substituted with one or more substituents Q. In certain embodiments, $R^6$ is monocyclic $C_{4-10}$ cycloalkyl, optionally substituted with one or more substituents Q. In certain embodiments, $R^6$ is cyclopropyl, cyclobutyl, cyclopentyl, cyclohexyl, or cycloheptyl, each optionally substituted with one or more substituents Q. In certain embodiments, $R^6$ is cyclopropyl, cyclobutyl, cyclopentyl, cyclohexyl, or cycloheptyl. In certain embodiments, $R^6$ is cyclopentyl, cyclohexyl, or cycloheptyl, each optionally substituted with one or more substituents Q. In certain embodiments, $R^6$ is cyclohexyl. In certain embodiments, $R^6$ is cyclopropyl. In certain embodiments, $R^6$ is $C_{6-14}$ aryl, optionally substituted with one or more substituents Q. In certain embodiments, $R^6$ is monocyclic $C_{6-14}$ aryl, optionally substituted with one or more substituents Q. In certain embodiments, $R^6$ is phenyl, optionally substituted with one or more substituents Q. In certain embodiments, $R^6$ is phenyl. In certain embodiments, $R^6$ is $C_{7-15}$ aralkyl, optionally substituted with one or more substituents Q. In certain embodiments, $R^6$ is heteroaryl, optionally substituted with one or more substituents Q. In certain embodiments, $R^6$ is monocyclic heteroaryl, optionally substituted with one or more substituents Q. In certain embodiments, $R^6$ is 5- or 6-membered heteroaryl, optionally substituted with one or more substituents Q. In certain embodiments, $R^6$ is heterocyclyl, optionally substituted with one or more substituents Q. In certain embodiments, $R^6$ is monocyclic heterocyclyl, optionally substituted with one or more substituents Q. In certain embodiments, $R^6$ is 5- or 6-membered heterocyclyl, optionally substituted with one or more substituents Q.

In one embodiment, provided herein is a compound selected from:
6-cyclohexyl-4-methylpyridine-2(1H)-thione A1;
4-methyl-6-(2,4,4-trimethylpentyl)pyridine-2(1H)-thione A2; and
6-cyclohexyl-4-trifluoromethylpyridine-2(1H)-thione A4;
and enantiomers, mixtures of enantiomers, tautomers, mixtures of two or more tautomers, and isotopic variants thereof; and pharmaceutically acceptable salts, solvates, hydrates, and prodrugs thereof.

In another embodiment, provided herein is a compound selected from:
6-cyclohexyl-4-methylpyridine-2(1H)-thione A1;
4-methyl-6-(2,4,4-trimethylpentyl)pyridine-2(1H)-thione A2;
6-cyclohexyl-4-trifluoromethylpyridine-2(1H)-thione A4;
6-isopropyl-4-methylpyridine-2(1H)-thione A5;
4-isopropyl-6-methylpyridine-2(1H)-thione A6; and
6-cyclopropyl-4-methylpyridine-2(1H)-thione A7;
and enantiomers, mixtures of enantiomers, tautomers, mixtures of two or more tautomers, and isotopic variants thereof; and pharmaceutically acceptable salts, solvates, hydrates, and prodrugs thereof.

In certain embodiments, a compound provided herein is deuterium-enriched. In certain embodiments, a compound provided herein is carbon-13 enriched. In certain embodiments, a compound provided herein is carbon-14 enriched. In certain embodiments, a compound provided herein contains one or more less prevalent isotopes for other elements, including, but not limited to, $^{15}N$ for nitrogen; $^{17}O$ or $^{18}O$ for oxygen, and $^{33}S$, $^{34}S$, or $^{36}S$ for sulfur.

In certain embodiments, a compound provided herein has an isotopic enrichment factor of no less than about 5, no less than about 10, no less than about 20, no less than about 30, no less than about 40, no less than about 50, no less than about 60, no less than about 70, no less than about 80, no less than about 90, no less than about 100, no less than about 200, no less than about 500, no less than about 1,000, no less than about 2,000, no less than about 5,000, or no less than about 10,000. In any events, however, an isotopic enrichment factor for a specified isotope is no greater than the maximum isotopic enrichment factor for the specified isotope, which is the isotopic enrichment factor when a compound at a given position is 100% enriched with the specified isotope. Thus, the maximum isotopic enrichment factor is different for different isotopes. The maximum isotopic enrichment factor is 6410 for deuterium and 90 for carbon-13.

In certain embodiments, a compound provided herein has a deuterium enrichment factor of no less than about 64 (about 1% deuterium enrichment), no less than about 130 (about 2% deuterium enrichment), no less than about 320 (about 5% deuterium enrichment), no less than about 640 (about 10% deuterium enrichment), no less than about 1,300 (about 20% deuterium enrichment), no less than about 3,200 (about 50% deuterium enrichment), no less than about 4,800 (about 75% deuterium enrichment), no less than about 5,130 (about 80% deuterium enrichment), no less than about 5,450 (about 85% deuterium enrichment), no less than about 5,770 (about 90% deuterium enrichment), no less than about 6,090 (about 95% deuterium enrichment), no less than about 6,220 (about 97% deuterium enrichment), no less than about 6,280 (about 98% deuterium enrichment), no less than about 6,350 (about 99% deuterium enrichment), or no less than about 6,380 (about 99.5% deuterium enrichment). The deuterium enrichment can be determined using conventional analytical methods known to one of ordinary skill in the art, including mass spectrometry and nuclear magnetic resonance spectroscopy.

In certain embodiments, a compound provided herein has a carbon-13 enrichment factor of no less than about 1.8 (about 2% carbon-13 enrichment), no less than about 4.5 (about 5% carbon-13 enrichment), no less than about 9 (about 10% carbon-13 enrichment), no less than about 18 (about 20% carbon-13 enrichment), no less than about 45 (about 50% carbon-13 enrichment), no less than about 68 (about 75% carbon-13 enrichment), no less than about 72 (about 80% carbon-13 enrichment), no less than about 77 (about 85% carbon-13 enrichment), no less than about 81 (about 90% carbon-13 enrichment), no less than about 86 (about 95% carbon-13 enrichment), no less than about 87 (about 97% carbon-13 enrichment), no less than about 88 (about 98% carbon-13 enrichment), no less than about 89 (about 99% carbon-13 enrichment), or no less than about 90 (about 99.5% carbon-13 enrichment). The carbon-13 enrichment can be determined using conventional analytical methods known to one of ordinary skill in the art, including mass spectrometry and nuclear magnetic resonance spectroscopy.

In certain embodiments, at least one of the atoms of a compound provided herein, as specified as isotopically enriched, has isotopic enrichment of no less than about 1%, no less than about 2%, no less than about 5%, no less than about 10%, no less than about 20%, no less than about 50%, no less than about 70%, no less than about 80%, no less than about 90%, or no less than about 98%. In certain embodiments, the atoms of a compound provided herein, as specified as isotopically enriched, have isotopic enrichment of no less than about 1%, no less than about 2%, no less than about 5%, no less than about 10%, no less than about 20%, no less than about 50%, no less than about 70%, no less than about 80%, no less than about 90%, or no less than about 98%. In any events, the isotopic enrichment of the isotopically enriched atom of a compound provided herein is no less than the natural abundance of the isotope specified.

In certain embodiments, at least one of the atoms of a compound provided herein, as specified as deuterium-enriched, has deuterium enrichment of no less than about 1%, no less than about 2%, no less than about 5%, no less than about 10%, no less than about 20%, no less than about 50%, no less than about 70%, no less than about 80%, no less than about 90%, or no less than about 98%. In certain embodiments, the atoms of a compound provided herein, as specified as deuterium-enriched, have deuterium enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, at least one of the atoms of a compound provided herein, as specified as $^{13}C$-enriched, has carbon-13 enrichment of no less than about 2%, no less than about 5%, no less than about 10%, no less than about 20%, no less than about 50%, no less than about 70%, no less than about 80%, no less than about 90%, or no less than about 98%. In certain embodiments, the atoms of a compound provided herein, as specified as $^{13}C$-enriched, have carbon-13 enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, a compound provided herein is isolated or purified. In certain embodiments, a compound provided herein has a purity of at least about 50%, at least about 70%, at least about 80%, at least about 90%, at least about 95%, at least about 98%, at least about 99%, or at least about 99.5% by weight.

The compounds provided herein are intended to encompass all possible stereoisomers, unless a particular stereochemistry is specified. Where a compound provided herein contains an alkenyl group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism. For example, a compound of Formula I can have at least the following tautomeric forms as shown below.

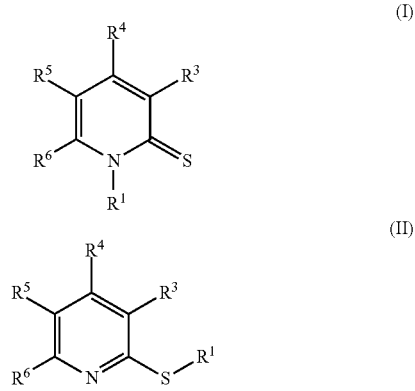

A compound provided herein can be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of ordinary skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When a compound provided herein contains an acidic or basic moiety, it can also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2011).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of a compound, for example, of Formula I and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, Controlled Drug Delivery 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

Methods of Synthesis

The compounds provided herein can be prepared, isolated, or obtained by any method known to one of ordinary skill in the art. In certain embodiments, a compound of Formula I is synthesized according to the synthetic procedures as shown in Scheme I. Compound 1 is treated with a thionating reagent to form a compound of Formula I.

Scheme I

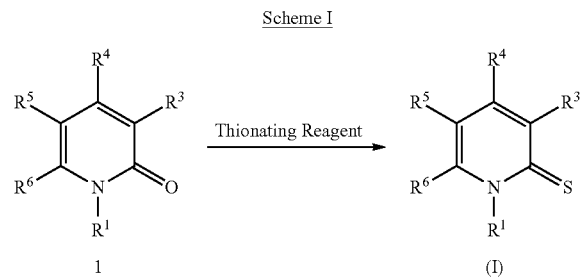

In certain embodiments, a compound of Formula I is synthesized according to the synthetic procedures as shown in Scheme II. Compound 2 or a salt thereof is treated with a thionating reagent to form a compound of Formula I.

Scheme II

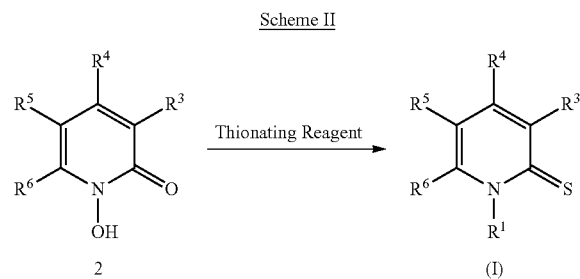

In certain embodiments, the thionating reagent is $P_2S_5$, Lawesson's reagent, Curphey's reagent ($P_4S_{10}$/hexamethyldisiloxane), Kaushik's reagent ($P_4S_{10}/Al_2O_3$), Bernthsen reagent ($S_8/I_2$), bis(trimethylsilyl)sulfide (HMDST), Heimgartner reagent, or Davy's reagent. Additional suitable thionating reagents include those described in Polshettiwar et al. *J. Sulfur Chem.* 2006, 27, 353-386.

Pharmaceutical Compositions

In one embodiment, provided herein is a pharmaceutical composition, comprising a compound of Formula I:

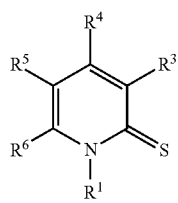

(I)

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient;

wherein:

$R^1$ is hydrogen or deuterium;

$R^3$ and $R^5$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(=N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(=N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^4$ is (i) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (ii) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, or —C(S)N$R^{1b}R^{1c}$;

$R^6$ is $C_{1-10}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(O)S$R^a$, —C(N$R^a$)N$R^bR^c$, —C(S)$R^a$, —C(S)O$R^a$, —C(S)N$R^bR^c$, —O$R^a$, —OC(O)$R^a$, —OC(O)O$R^a$, —OC(O)N$R^bR^c$, —OC(O)S$R^a$, —OC(=N$R^a$)N$R^bR^c$, —OC(S)$R^a$, —OC(S)O$R^a$, —OC(S)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(O)S$R^d$, —N$R^a$C(=N$R^d$)N$R^bR^c$, —N$R^a$C(S)$R^d$, —N$R^a$C(S)O$R^d$, —N$R^a$C(S)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from: (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(O)SR$^e$, —C(NR$^e$)NR$^f$R$^g$, —C(S)R$^e$, —C(S)OR$^e$, —C(S)NR$^f$R$^g$, —OR$^e$, —OC(O)R$^e$, —OC(O)OR$^e$, —OC(O)NR$^f$R$^g$, —OC(O)SR$^e$, —OC(=NR$^e$)NR$^f$R$^g$, —OC(S)R$^e$, —OC(S)OR$^e$, —OC(S)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(O)SR$^f$, —NR$^e$(=NR$^h$)NR$^f$R$^g$, —NR$^e$C(S)R$^h$, —NR$^e$C(S)OR$^f$, —NR$^e$C(S)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

In another embodiment, provided herein is a pharmaceutical composition, comprising a compound selected from:
6-cyclohexyl-4-methylpyridine-2(1H)-thione A1;
4-methyl-6-(2,4,4-trimethylpentyl)pyridine-2(1H)-thione A2;
6-methyl-4-trifluoromethylpyridine-2(1H)-thione A3; and
6-cyclohexyl-4-trifluoromethylpyridine-2(1H)-thione A4;
and enantiomers, mixtures of enantiomers, tautomers, mixtures of two or more tautomers, and isotopic variants thereof; and pharmaceutically acceptable salts, solvates, hydrates, and prodrugs thereof; and a pharmaceutically acceptable excipient.

In yet another embodiment, provided herein is a pharmaceutical composition, comprising a compound selected from:
6-cyclohexyl-4-methylpyridine-2(1H)-thione A1;
4-methyl-6-(2,4,4-trimethylpentyl)pyridine-2(1H)-thione A2;
6-methyl-4-trifluoromethylpyridine-2(1H)-thione A3;
6-cyclohexyl-4-trifluoromethylpyridine-2(1H)-thione A4;
6-isopropyl-4-methylpyridine-2(1H)-thione A5;
4-isopropyl-6-methylpyridine-2(1H)-thione A6; and
6-cyclopropyl-4-methylpyridine-2(1H)-thione A7;
and enantiomers, mixtures of enantiomers, tautomers, mixtures of two or more tautomers, and isotopic variants thereof; and pharmaceutically acceptable salts, solvates, hydrates, and prodrugs thereof; and a pharmaceutically acceptable excipient.

The compound provided herein may be administered alone, or in combination with one or more other compounds provided herein. The pharmaceutical compositions that comprise a compound provided herein, e.g., a compound of Formula I, can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology*, 2nd Edition, Rathbone et al., Eds., Marcel Dekker, Inc.: New York, N.Y., 2008).

In one embodiment, a pharmaceutical composition provided herein is formulated in a dosage form for oral administration, which comprises a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

In another embodiment, a pharmaceutical composition provided herein is formulated as a suspension for oral administration, which comprises a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient. In one embodiment, the suspension provided herein comprises a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and one or more pharmaceutically acceptable excipients selected from: water, glycerin, sorbitol, sodium saccharin, xanthan gum, flavoring, citric acid, sodium citrate, methylparaben, propylparaben, and potassium sorbate. In another embodiment, the suspension provided herein comprises a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and water, glycerin, sorbitol, sodium saccharin, xanthan gum, flavoring, citric acid, sodium citrate, methylparaben, propylparaben, and potassium sorbate.

In yet another embodiment, a pharmaceutical composition provided herein is formulated in a dosage form for parenteral administration, which comprises a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient. In one embodiment, a pharmaceutical composition provided herein is formulated in a dosage form for intravenous administration. In another embodiment, a pharmaceutical composition provided herein is formulated in a dosage form for intramuscular administration. In yet another embodiment, a pharmaceutical composition provided herein is formulated in a dosage form for subcutaneous administration.

In yet another embodiment, a pharmaceutical composition provided herein is formulated in a dosage form for topical administration, which comprise a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient.

In one embodiment, a pharmaceutical composition provided herein is formulated as a cream for topical administration, which comprises a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient. In one embodiment, the cream provided herein comprises a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and one or more pharmaceutically acceptable excipients selected from: water, octyldodecanol, mineral oil, stearyl alcohol, cocamide DEA, polysorbate 60, myristyl alcohol, sorbitan monostearate, lactic acid, and benzyl alcohol. In another embodiment, the cream provided herein comprises a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and water, octyldodecanol, mineral oil, stearyl alcohol, cocamide DEA, polysorbate 60, myristyl alcohol, sorbitan monostearate, lactic acid, and benzyl alcohol.

In another embodiment, a pharmaceutical composition provided herein is formulated as a gel for topical administration, which comprises a compound provided herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, and a pharmaceutically acceptable excipient. In one embodiment, the gel provided herein comprises a compound provided herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, and one or more pharmaceutically acceptable excipients selected from: water, isopropyl alcohol, octyldodecanol, dimethicone copolyol 190, carbomer 980, sodium hydroxide, and docusate sodium. In another embodiment, the gel provided herein comprises a compound provided herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, and water, isopropyl alcohol, octyldodecanol, dimethicone copolyol 190, carbomer 980, sodium hydroxide, and docusate sodium.

In yet another embodiment, a pharmaceutical composition provided herein is formulated as a shampoo for topical administration, which comprises a compound provided herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, and a pharmaceutically acceptable excipient. In one embodiment, the shampoo provided herein comprises a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and one or more pharmaceutically acceptable excipients selected from: water, sodium laureth sulfate, disodium laureth sulfosuccinate, sodium chloride, and laureth-2. In another embodiment, the shampoo provided herein comprises a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and water, sodium laureth sulfate, disodium laureth sulfosuccinate, sodium chloride, and laureth-2.

In still another embodiment, a pharmaceutical composition provided herein is formulated as a lacquer for topical administration, which comprises a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and a pharmaceutically acceptable excipient. In one embodiment, the lacquer provided herein comprises a compound provided herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof; and one or more pharmaceutically acceptable excipients selected from: ethyl acetate, isopropyl alcohol, and butyl monoester of poly(methylvinyl ether/maleic acid) in isopropyl alcohol. In another embodiment, the lacquer provided herein comprises a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; and ethyl acetate, isopropyl alcohol, and butyl monoester of poly(methylvinyl ether/maleic acid) in isopropyl alcohol.

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; algins; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber, epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Phar-* macy, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as I-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324;

6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form can be fabricated using a matrix controlled release device known to those skilled in the art (see, Takada et al. in "Encyclopedia of Controlled Drug Delivery," Vol. 2, Mathiowitz Ed., Wiley, 1999).

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided herein is a method for treating one or more symptoms of a proliferative, inflammatory, neurodegenerative, or immune-mediated disease, in one embodiment, multiple sclerosis, in a subject, comprising administering to the subject a compound of Formula I:

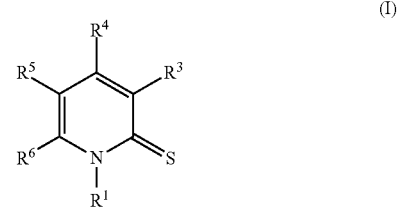

or an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof; wherein:

$R^1$ is hydrogen or deuterium;

$R^3$ and $R^5$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, —C(S)N$R^{1b}R^{1c}$, —O$R^{1a}$, —OC(O)$R^{1a}$, —OC(O)O$R^{1a}$, —OC(O)N$R^{1b}R^{1c}$, —OC(O)S$R^{1a}$, —OC(=N$R^{1a}$)N$R^{1b}R^{1c}$, —OC(S)$R^{1a}$, —OC(S)O$R^{1a}$, —OC(S)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(O)S$R^{1d}$, —N$R^{1a}$C(=N$R^{1d}$)N$R^{1b}R^{1c}$, —N$R^{1a}$C(S)$R^{1d}$, —N$R^{1a}$C(S)O$R^{1d}$, —N$R^{1a}$C(S)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^4$ is (i) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (ii) —C(O)$R^{1a}$, —C(O)O$R^{1a}$, —C(O)N$R^{1b}R^{1c}$, —C(O)S$R^{1a}$, —C(N$R^{1a}$)N$R^{1b}R^{1c}$, —C(S)$R^{1a}$, —C(S)O$R^{1a}$, or —C(S)N$R^{1b}R^{1c}$;

$R^6$ is $C_{1-10}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more, in one embodiment, one, two, three, or four, substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(O)S$R^a$, —C(N$R^a$)N$R^bR^c$, —C(S)$R^a$, —C(S)O$R^a$, —C(S)N$R^bR^c$, —O$R^a$, —OC(O)$R^a$, —OC(O)O$R^a$, —OC(O)N$R^bR^c$, —OC(O)S$R^a$, —OC(=N$R^a$)N$R^bR^c$, —OC(S)$R^a$, —OC(S)O$R^a$, —OC(S)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(O)S$R^d$, —N$R^a$C(=N$R^d$)N$R^bR^c$, —N$R^a$C(S)$R^d$, —N$R^a$C(S)O$R^d$, —N$R^a$C(S)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from: (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(O)S$R^e$, —C(N$R^e$)N$R^fR^g$, —C(S)$R^e$, —C(S)O$R^e$, —C(S)N$R^fR^g$, —O$R^e$, —OC(O)$R^e$, —OC(O)O$R^e$, —OC(O)N$R^fR^g$, —OC(O)S$R^e$, —OC(=N$R^e$)N$R^fR^g$, —OC(S)$R^e$, —OC(S)O$R^e$, —OC(S)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^f$, —N$R^e$C(O)N$R^fR^g$, —N$R^e$C(O)S$R^f$, —N$R^e$C(=N$R^h$)N$R^fR^g$, —N$R^e$C(S)$R^h$, —N$R^e$C(S)O$R^f$, —N$R^e$C(S)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In another embodiment, provided herein is a method for treating one or more symptoms of a proliferative, inflammatory, neurodegenerative, or immune-mediated disease, in one embodiment, multiple sclerosis, in a subject, comprising administering to the subject a compound selected from:

6-cyclohexyl-4-methylpyridine-2(1H)-thione A1;
4-methyl-6-(2,4,4-trimethylpentyl)pyridine-2(1H)-thione A2;
6-methyl-4-trifluoromethylpyridine-2(1H)-thione A3; and
6-cyclohexyl-4-trifluoromethylpyridine-2(1H)-thione A4;
and enantiomers, mixtures of enantiomers, tautomers, mixtures of two or more tautomers, and isotopic variants thereof; and pharmaceutically acceptable salts, solvates, hydrates, and prodrugs thereof.

In yet another embodiment, provided herein is a method for treating one or more symptoms of a proliferative, inflammatory, neurodegenerative, or immune-mediated disease, in one embodiment, multiple sclerosis, in a subject, comprising administering to the subject a compound selected from:

6-cyclohexyl-4-methylpyridine-2(1H)-thione A1;
4-methyl-6-(2,4,4-trimethylpentyl)pyridine-2(1H)-thione A2;
6-methyl-4-trifluoromethylpyridine-2(1H)-thione A3;
6-cyclohexyl-4-trifluoromethylpyridine-2(1H)-thione A4;
6-isopropyl-4-methylpyridine-2(1H)-thione A5;
4-isopropyl-6-methylpyridine-2(1H)-thione A6; and
6-cyclopropyl-4-methylpyridine-2(1H)-thione A7;
and enantiomers, mixtures of enantiomers, tautomers, mixtures of two or more tautomers, and isotopic variants thereof; and pharmaceutically acceptable salts, solvates, hydrates, and prodrugs thereof.

In one embodiment, provided herein is a method for treating a proliferative disease in a subject, which comprises administering to the subject a therapeutically effective amount of a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In another embodiment, provided herein is a method for treating an inflammatory disease in a subject, which comprises administering to the subject a therapeutically effective amount of a compound provided herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof.

In yet another embodiment, provided herein is a method for treating a neurodegenerative disease in a subject, which comprises administering to the subject a therapeutically effective amount of a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In yet another embodiment, provided herein is a method for treating an immune-mediated disease in a subject, which comprises administering to the subject a therapeutically effective amount of a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In certain embodiments, the therapeutically effective amount is ranging from about 0.1 to about 100 mg/kg/day, from about 0.1 to about 50 mg/kg/day, from about 0.1 to about 40 mg/kg/day, from about 0.1 to about 30 mg/kg/day, from about 0.1 to about 25 mg/kg/day, from about 0.1 to about 20 mg/kg/day, from about 0.1 to about 15 mg/kg/day, from about 0.1 to about 10 mg/kg/day, or from about 0.1 to about 5 mg/kg/day. In one embodiment, the therapeutically effective amount is ranging from about 0.1 to about 100 mg/kg/day. In another embodiment, the therapeutically effective amount is ranging from about 0.1 to about 50 mg/kg/day. In yet another embodiment, the therapeutically effective amount is ranging from about 0.1 to about 40 mg/kg/day. In yet another embodiment, the therapeutically effective amount is ranging from about 0.1 to about 30 mg/kg/day. In yet another embodiment, the therapeutically effective amount is ranging from about 0.1 to about 25 mg/kg/day. In yet another embodiment, the therapeutically effective amount is ranging from about 0.1 to about 20 mg/kg/day. In yet another embodiment, the therapeutically effective amount is ranging from about 0.1 to about 15 mg/kg/day. In yet another embodiment, the therapeutically effective amount is ranging from about 0.1 to about 10 mg/kg/day. In still another embodiment, the therapeutically effective amount is ranging from about 0.1 to about 5 mg/kg/day.

It is understood that the administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both. For example, a dose of 1 mg/m$^2$/day for a 65 kg human is approximately equal to 38 mg/kg/day.

In certain embodiments, the subject is a mammal. In certain embodiments, the subject is a human.

In certain embodiments, the diseases that are treatable with the methods provided herein include, but are not limited to, chronic active hepatitis (CAH), primary biliary cirrhosis (PBC), primary sclerosing cholangitis (PSC), celiac disease, pernicious anemia, and inflammatory bowel disease.

In certain embodiments, the diseases that are treatable with the methods provided herein include, but are not limited to, chronic inflammatory demyelinating polyradiculoneuropathy (CIDP), acute inflammatory demyelinating polyneuropathy (AIDP), Lambert-Eaton myasthenic syndrome (LEMS), myasthenia gravis, meuromyotonia (Isaacs' syndrome), stiff man syndrome or Moersch-Woltmann syndrome, multiple sclerosis (MS), Gullain-Barre syndrome, multifocal motor neuropathy with conduction block (MMN), monoclonal gammopathy, paraneoplastic neurological disorders (PND's), Oppsoclonus-myoclonus syndrome (OMS), encephalomyelitis, and autoimmune retinopathy (AR) (recoverin-associated retinopathy (RAR)).

In certain embodiments, the diseases that are treatable with the methods provided herein include, but are not limited to, systemic necrotizing vascolitides, polyarteritis nodosa (PAN), polymyalgia rheumatic, Churg-Strauss syndrome (CSS), allergic granulomatosis angiitis, hypersensitivity vasculitis, Wegener's, granulomatosis, temporal arteritis, giant cell arteritis (GCV), Takayasu's arteritis (TAK), Kawasaki disease (KD), isolated vasculitis of the central nervous system, CNS vasculitis, thromboangiitis obliterans, Buerger's disease, sarcoidosis, graft-versus-host disease (GVHD), cryoglobulinemia, and cryopathies.

In certain embodiments, the diseases that are treatable with the methods provided herein include, but are not limited to, Meniere's disease, Raynaud's phenomenon, antiphospholipid syndrome (APS), autoimmune lymphoproliferative syndrome (ALPS), autoimmune inner ear disease (AIED), and Cogan's syndrome.

In certain embodiments, the diseases that are treatable with the methods provided herein include, but are not limited to, alopecia areata, autoimmune hemolytic anemia, autoimmune hepatitis, cerebral palsy, dermatomyositis, diabetes (type 1), certain juvenile idiopathic arthritis, glomerulonephritis, Graves' disease, Guilain-Barre syndrome, idiopathic thrombocytopenic purpura, myasthenia gravis, certain myocarditis, multiple sclerosis, pemphigus/pemphigoid, pernicious anemia, polyarteritis nodosa, polymyositis, primary biliary cirrhosis, psoriatic arthritis, psoriasis, rheumatoid arthritis, schleroderma/systemic sclerosis, Sjogren's syndrome, systemic lupus erythematosus, certain thyroiditis, certain uveitis, vitiligo, and granulomatosis with polyangiitis (Wegener's).

In certain embodiments, the diseases that are treatable with the methods provided herein include, but are not limited to, spinal cord degeneration as a result of metabolic cobalamin deficiency, demyelination disease, an inflammatory demyelination disease, a non-inflammatory demyelination disease, an ischemic injury to the brain, stroke, or a concussive injury. In certain embodiments, the non-inflammatory demyelination disease is multiple sclerosis. In certain embodiments, the non-inflammatory demyelination disease is relapsing-remitting MS (RR-MS), primary progressive MS (PP-MS), progressive relapsing MS (PR-MS), or secondary progressive MS (SP-MS).

In certain embodiments, the disease that is treatable with a method provided herein is a proliferative disease. In certain embodiments, the disease that is treatable with a method provided herein is an inflammatory disease. In certain embodiments, the disease that is treatable with a method provided herein is a neurodegenerative disease. In certain embodiments, the disease that is treatable with a method provided herein is an immune-mediated disease.

In certain embodiments, the immune-mediated disease is an inflammatory disease or disorder related to immune dysfunction, immunodeficiency, or immunomodulation, including, but not limited to, autoimmune diseases, tissue transplant rejection, graft-versus-host disease, wound healing, kidney disease, multiple sclerosis, thyroiditis, type 1 diabetes, sarcoidosis, allergic rhinitis, inflammatory bowel diseases (including Crohn's disease and ulcerative colitis (UC)), systemic lupus erythematosis (SLE), arthritis, osteoarthritis, rheumatoid arthritis, osteoporosis, asthma, and chronic obstructive pulmonary disease (COPD).

In certain embodiments, the immune-mediated disease is an autoimmune disease. In certain embodiments, the autoimmune is a B cell-mediated autoimmune disease. In certain embodiments, the autoimmune disease is an antibody-mediated autoimmune disease. In certain embodiments, the autoimmune disease is a T-cell mediated autoimmune disease.

In certain embodiments, the autoimmune disease is alopecia areata, autoimmune hemolytic anemia, autoimmune hepatitis, dermatomyositis, diabetes (type 1), certain juvenile idiopathic arthritis, glomerulonephritis, Graves' disease, Guilain-Barre syndrome, idiopathic thrombocytopenic purpura, myasthenia gravis, certain myocarditis, multiple sclerosis, pemphigus/pemphigoid, pernicious anemia, polyarteritis nodosa, polymyositis, primary biliary cirrhosis, psoriatic arthritis, psoriasis, rheumatoid arthritis, schleroderma/systemic sclerosis, Sjogren's syndrome, systemic lupus erythematosus, certain thyroiditis, certain uveitis, vitiligo, or granulomatosis with polyangiitis (Wegener's).

In certain embodiments, the autoimmune disease is multiple sclerosis (MS). In certain embodiments, the autoimmune disease is relapsing-remitting MS (RR-MS). In certain embodiments, the autoimmune disease is primary progressive MS (PP-MS). In certain embodiments, the autoimmune disease is progressive relapsing MS (PR-MS). In certain embodiments, the autoimmune disease is secondary progressive MS (SP-MS).

In certain embodiments, the autoimmune disease is neuromyelitis optica (NMO), NMO spectrum disorder (NMOSD), or Devic's disease.

In certain embodiments, the proliferative disease is a carcinoma, including, but not limited to, Kit-mediated carcinomas, adenocarcinoma, squamous cell carcinoma, adenosquamous carcinoma, teratocarcinoma, head and neck cancer, brain cancer, intracranial carcinoma, glioblastoma (including PDGFR-mediated glioblastoma), glioblastoma multiforme (including PDGFR-mediated glioblastoma multiforme), neuroblastoma, cancer of the larynx, multiple endocrine neoplasias 2A and 2B (MENS 2A and MENS 2B) (including RET-mediated MENS), thyroid cancer (including sporadic and familial medullary thyroid carcinoma), papillary thyroid carcinoma, parathyroid carcinoma (including any RET-mediated thyroid carcinoma), follicular thyroid cancer, anaplastic thyroid cancer, bronchial carcinoid, oat cell carcinoma, lung cancer, small-cell lung cancer (including FLT3 and/or Kit-mediated small cell lung cancer), stomach/gastric cancer, gastrointestinal cancer, gastrointestinal stromal tumors (GIST) (including Kit-mediated GIST and PDGFR α-mediated GIST), colon cancer, colorectal cancer, pancreatic cancer, islet cell carcinoma, hepatic/liver cancer, metastases to the liver, bladder cancer, renal cell cancer (including PDGFR-mediated renal cell cancer), cancers of the genitourinary tract, ovarian cancer (including Kit-mediated and/or PDGFR-mediated ovarian cancer), endometrial cancer (including CSF-1R-mediated endometrial cancer), cervical cancer, breast cancer (including FLT3-mediated and/or PDGFR-mediated breast cancer), prostate cancer (including Kit-mediated prostate cancer), germ cell tumors (including Kit-mediated germ cell tumors), seminomas (including Kit-mediated seminomas), dysgerminomas (including Kit-mediated dysgerminomas), melanoma (including PDGFR-mediated melanoma), metastases to the bone (including CSF-1R-mediated bone metastases), metastatic tumors (including VEGFR-mediated tumors), stromal tumors, neuroendocrine tumors, tumor angiogenesis (including VEGFR-mediated tumor angiogenesis), and mixed mesodermal tumors.

In certain embodiments, the proliferative disease is sarcomas, including, but not limited to, PDGFR-mediated sarcomas, osteosarcoma, osteogenic sarcoma, bone cancer, glioma (including PDGFR-mediated and/or CSF-1R-mediated glioma), astrocytoma, vascular tumors (including VEGFR-mediated vascular tumors), Kaposi's sarcoma, carcinosarcoma, hemangiosarcomas (including VEGFR3-mediated hemangiosarcomas), and lymphangiosarcoma (including VEGFR3-mediated lymphangiosarcoma).

In certain embodiments, the proliferative disease is a hematologic malignancy. In certain embodiments, the proliferative disease is a relapsed hematologic malignancy. In certain embodiments, the proliferative disease is a refractory hematologic malignancy. In certain embodiments, the proliferative disease is a drug-resistant hematologic malignancy. In certain embodiments, the proliferative disease is a multidrug-resistant hematologic malignancy. In certain embodiments, the proliferative disease is a Bcr-Abl kinase inhibitor-resistant hematologic malignancy. In certain embodiments, the proliferative disease is an imatinib-resistant hematologic malignancy. In certain embodiments, the proliferative disease is a dasatinib-resistant hematologic malignancy. In certain embodiments, the proliferative disease is a nilatinib-resistant hematologic malignancy. In certain embodiments, the proliferative disease is a bosutinib-resistant hematologic malignancy. In certain embodiments, the proliferative disease is a cytarabine-resistant hematologic malignancy.

In certain embodiments, the hematologic malignancy is myeloma, leukemia, myeloproliferative diseases, acute myeloid leukemia (AML) (including FLT3 mediated and/or KIT-mediated and/or CSF1R-mediated acute myeloid leukemia), chronic myeloid leukemias (CML) (including FLT3-mediated and/or PDGFR-mediated chronic myeloid leukemia), myelodysplastic leukemias (including FLT3-mediated myelodysplastic leukemia), myelodysplastic syndrome (including FLT3 mediated and/or Kit-mediated myelodysplastic syndrome), idiopathic hypereosinophilic syndrome (HES) (including PDGFR-mediated HES), chronic eosinophilic leukemia (CEL) (including PDGFR-mediated CEL), chronic myelomonocytic leukemia (CMML), mast cell leukemia (including Kit-mediated mast cell leukemia), or systemic mastocytosis (including Kit-mediated systemic mastocytosis).

In certain embodiments, the hematologic malignancy is lymphoma, lymphoproliferative diseases, acute lymphoblastic leukemia (ALL), B-cell acute lymphoblastic leukemias, T-cell acute lymphoblastic leukemias, chronic lymphocytic leukemia (CLL), natural killer (NK) cell leukemia, B-cell lymphoma, T-cell lymphoma, or natural killer (NK) cell lymphoma.

In certain embodiments, the hematologic malignancy is Langerhans cell histiocytosis (including CSF-1R-mediated and/or FLT3-mediated Langerhans cell histiocytosis), mast cell tumors, or mastocytosis.

In certain embodiments, the hematologic malignancy is leukemia. In certain embodiments, the hematologic malignancy is relapsed leukemia. In certain embodiments, the hematologic malignancy is refractory leukemia. In certain embodiments, the hematologic malignancy is drug-resistant leukemia. In certain embodiments, the hematologic malignancy is multidrug-resistant leukemia. In certain embodiments, the hematologic malignancy is a Bcr-Abl kinase inhibitor-resistant leukemia. In certain embodiments, the hematologic malignancy is imatinib-resistant leukemia. In certain embodiments, the hematologic malignancy is dasatinib-resistant leukemia. In certain embodiments, the hematologic malignancy is nilatinib-resistant leukemia. In certain embodiments, the hematologic malignancy is bosutinib-resistant leukemia. In certain embodiments, the hematologic malignancy is cytarabine-resistant leukemia.

In certain embodiments, the leukemia is acute leukemia. In certain embodiments, the leukemia is relapsed acute leukemia. In certain embodiments, the leukemia is refractory acute leukemia. In certain embodiments, the leukemia is drug-resistant acute leukemia. In certain embodiments, the leukemia is multidrug-resistant acute leukemia. In certain embodiments, the leukemia is a Bcr-Abl kinase inhibitor-resistant acute leukemia. In certain embodiments, the leukemia is imatinib-resistant acute leukemia. In certain embodiments, the leukemia is dasatinib-resistant acute leukemia. In certain embodiments, the leukemia is nilatinib-resistant acute leukemia. In certain embodiments, the leukemia is bosutinib-resistant acute leukemia. In certain embodiments, the leukemia is cytarabine-resistant acute leukemia. In certain embodiments, the leukemia is a hereditary leukemia. In certain embodiments, the hereditary leukemia is severe congenital neutropenia (SCN). In certain embodiments, the hereditary leukemia is familial platelet disorder with acute myelogenous leukemia (FDP/AML). In certain embodiments, the leukemia is caused by LEF1. In certain embodiments, the leukemia is mediated by LEF1. In certain embodiments, the leukemia is caused by GSK3.

In certain embodiments, the leukemia is ALL. In certain embodiments, the leukemia is relapsed ALL. In certain embodiments, the leukemia is refractory ALL. In certain embodiments, the leukemia is drug-resistant ALL. In certain embodiments, the leukemia is multidrug-resistant ALL. In certain embodiments, the leukemia is a Bcr-Abl kinase inhibitor-resistant ALL. In certain embodiments, the leukemia is imatinib-resistant ALL. In certain embodiments, the leukemia is dasatinib-resistant ALL. In certain embodiments, the leukemia is nilatinib-resistant ALL. In certain embodiments, the leukemia is bosutinib-resistant ALL. In certain embodiments, the leukemia is cytarabine-resistant ALL.

In one embodiment, ALL is leukemia that originates in the blast cells of the bone marrow (B-cells), thymus (T-cells), or lymph nodes. ALL is categorized according to the French-American-British (FAB) Morphological Classification Scheme as L1—mature-appearing lymphoblasts (T-cells or pre-B-cells), L2—immature and pleomorphic (variously shaped) lymphoblasts (T-cells or pre-B-cells), and L3—lymphoblasts (B-cells; Burkitt's cells). In another embodiment, ALL originates in the blast cells of the bone marrow (B-cells). In yet another embodiment, ALL originates in the thymus (T-cells). In yet another embodiment, ALL originates in the lymph nodes. In yet another embodiment, ALL is L1 type characterized by mature-appearing lymphoblasts (T-cells or pre-B-cells). In yet another embodiment, ALL is L2 type characterized by immature and pleomorphic (variously shaped) lymphoblasts (T-cells or pre-B-cells). In still another embodiment, ALL is L3 type characterized by lymphoblasts (B-cells; Burkitt's cells).

In certain embodiments, the leukemia is AML. In certain embodiments, the leukemia is relapsed AML. In certain embodiments, the leukemia is refractory AML. In certain embodiments, the leukemia is drug-resistant AML. In certain embodiments, the leukemia is multidrug-resistant AML. In certain embodiments, the leukemia is a Bcr-Abl kinase inhibitor-resistant AML. In certain embodiments, the leukemia is imatinib-resistant AML. In certain embodiments, the leukemia is dasatinib-resistant AML. In certain embodiments, the leukemia is nilatinib-resistant AML. In certain embodiments, the leukemia is bosutinib-resistant AML. In certain embodiments, the leukemia is cytarabine-resistant AML. In certain embodiments, AML has a RAS mutation. In certain embodiments, the RAS mutation is NRAS, KRAS, or HRAS. In certain embodiments, the RAS mutation is NRAS. In certain embodiments, the RAS mutation is KRAS. In certain embodiments, the RAS mutation is HRAS.

In certain embodiments, AML is undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), or megakaryoblastic leukemia (M7). In one embodiment, AML is undifferentiated AML (M0). In another embodiment, AML is myeloblastic leukemia (M1). In yet another embodiment, AML is myeloblastic leukemia (M2). In yet another embodiment, AML is promyelocytic leukemia (M3 or M3 variant [M3V]). In yet another embodiment, AML is myelomonocytic leukemia (M4 or M4 variant with eosinophilia [M4E]). In yet another embodiment, AML is monocytic leukemia (M5). In yet another embodiment, AML is erythroleukemia (M6). In still another embodiment, AML is megakaryoblastic leukemia (M7).

In certain embodiments, the leukemia is chronic leukemia. In certain embodiments, the leukemia is relapsed chronic leukemia. In certain embodiments, the leukemia is refractory chronic leukemia. In certain embodiments, the leukemia is drug-resistant chronic leukemia. In certain embodiments, the leukemia is multidrug-resistant chronic leukemia. In certain embodiments, the leukemia is a Bcr-Abl kinase inhibitor-resistant chronic leukemia. In certain embodiments, the leukemia is imatinib-resistant chronic leukemia. In certain embodiments, the leukemia is dasatinib-resistant chronic leukemia. In certain embodiments, the leukemia is nilatinib-resistant chronic leukemia. In certain embodiments, the leukemia is bosutinib-resistant chronic leukemia. In certain embodiments, the leukemia is cytarabine-resistant chronic leukemia.

In certain embodiments, the leukemia is CLL. In certain embodiments, the leukemia is relapsed CLL. In certain embodiments, the leukemia is refractory CLL. In certain embodiments, the leukemia is drug-resistant CLL. In certain embodiments, the leukemia is multidrug-resistant CLL. In certain embodiments, the leukemia is a Bcr-Abl kinase inhibitor-resistant CLL. In certain embodiments, the leukemia is imatinib-resistant CLL. In certain embodiments, the leukemia is dasatinib-resistant CLL. In certain embodiments, the leukemia is nilatinib-resistant CLL. In certain embodiments, the leukemia is bosutinib-resistant CLL. In certain embodiments, the leukemia is cytarabine-resistant CLL.

In certain embodiments, the leukemia is CML. In certain embodiments, the leukemia is relapsed CML. In certain embodiments, the leukemia is refractory CML. In certain embodiments, the leukemia is drug-resistant CML. In certain embodiments, the leukemia is multidrug-resistant CML. In certain embodiments, the leukemia is a Bcr-Abl kinase inhibitor-resistant CML. In certain embodiments, the leukemia is imatinib-resistant CML. In certain embodiments, the leukemia is dasatinib-resistant CML. In certain embodiments, the leukemia is nilatinib-resistant CML. In certain embodiments, the leukemia is bosutinib-resistant CML. In certain embodiments, the leukemia is cytarabine-resistant CML. In certain embodiments, the leukemia is juvenile CML. In certain embodiments, the leukemia is juvenile CML with one or more NF-1 mutations.

In certain embodiments, the leukemia is T-cell leukemia. In one embodiment, the T-cell leukemia is peripheral T-cell leukemia, T-cell lymphoblastic leukemia, cutaneous T-cell leukemia, and adult T-cell leukemia. In another embodiment, the T-cell leukemia is peripheral T-cell leukemia. In yet another embodiment, the T-cell leukemia is T-cell lymphoblastic leukemia. In yet another embodiment, the T-cell leukemia is cutaneous T-cell leukemia. In still another embodiment, the T-cell leukemia is adult T-cell leukemia.

In certain embodiments, the leukemia is Philadelphia positive. In one embodiment, the Philadelphia positive leukemia is Philadelphia positive AML, including, but not limited to, undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), or megakaryoblastic leukemia (M7). In another embodiment, the Philadelphia positive leukemia is Philadelphia positive ALL.

In certain embodiments, the proliferative disease is cancer, including, but not limited to, head and neck cancer (originating lip, oral cavity, oropharynx, hypopharynx, larynx, nasopharynx, nasal cavity, paranasal sinuses, or salivary glands), lung cancer (including small cell lung cancer and non-small cell lung cancer), gastrointestinal tract cancers (including esophageal cancer), gastric cancer, colorectal cancer, anal cancer, pancreatic cancer, liver cancer, gallbladder cancer, extrahepatic bile duct cancer, cancer of the ampulla of vater, breast cancer, gynecologic cancers (including cancer of uterine cervix), cancer of the uterine body, vaginal cancer, vulvar cancer, ovarian cancer, gestational trophoblastic cancer neoplasia, testicular cancer, urinary tract cancers (including renal cancer), urinary bladder cancer, prostate cancer, penile cancer, urethral cancer, neurologic tumors, endocrine neoplasms (including carcinoid and islet cell tumors), pheochromocytoma, adrenal cortical carcinoma, parathyroid carcinoma and metastases to endocrine glands.

Further examples of cancers are basal cell carcinoma, squamous cell carcinoma, chondrosarcoma (a cancer arising in cartilage cells), mesenchymal-chondrosarcoma, soft tissue sarcomas (including malignant tumors that may arise in any of the mesodermal tissues (muscles, tendons, vessels that carry blood or lymph, joints and fat)), soft tissue sarcomas (include alveolar soft-part sarcoma), angiosarcoma, fibrosarcoma, leiomyosarcoma, liposarcoma, malignant fibrous histiocytoma, hemangiopericytoma, mesenchymoma, schwannoma, peripheral neuroectodermal tumours, rhabdomyosarcoma, synovial sarcoma, gestational trophoblastic tumor (malignancy in which the tissues formed in the uterus following conception become cancerous), Hodgkin's lymphoma, and laryngeal cancer.

In certain embodiments, the proliferative disease is a nonmalignant proliferation disease, including, but not limited to, atherosclerosis (including PDGFR-mediated atherosclerosis), restenosis following vascular angioplasty (including PDGFR-mediated restenosis), and fibroproliferative disorders (including obliterative bronchiolitis and idiopathic myelofibrosis).

In certain embodiments, the proliferative disease is an inflammatory disease or disorder related to immune dysfunction, immunodeficiency, or immunomodulation, including, but not limited to, autoimmune diseases, tissue transplant rejection, graft-versus-host disease, wound healing, kidney disease, multiple sclerosis, thyroiditis, type 1 diabetes, sarcoidosis, allergic rhinitis, inflammatory bowel diseases (including Crohn's disease and ulcerative colitis (UC)), systemic lupus erythematosis (SLE), arthritis, osteoarthritis, rheumatoid arthritis, osteoporosis, asthma, and chronic obstructive pulmonary disease (COPD).

In certain embodiments, the proliferative disease is an infectious disease. In certain embodiments, the infectious disease is fungal infection. In certain embodiments, the infectious disease is a superficial mycose (e.g., *Tinea versicolor*). In certain embodiments, the infectious disease is a cutaneous mycose (e.g., epidermis). In certain embodiments, the infectious disease is a subcutaneous mycose. In certain embodiments, the infectious disease is a systemic mycose.

In certain embodiments, the proliferative disease is leukemia, adult T-cell leukemia, promyelocytic leukemia, pre-B cell leukemia, lymphoma, Mantle cell lymphoma, breast cancer, pancreatic cancer, prostate cancer, head and neck cancer, ovarian cancer, melanoma, giloma, liver cancer, renal cancer, colorectal cancer, rhabdomyosarcoma, tongue cancer, stomach cancer, multiple myeloma, bladder cancer, thyroid cancer, epidermoid carcinoma, lung cancer, NSC lung cancer, or large cell lung cancer.

In certain embodiments, the proliferative disease is adult T-cell leukemia, promyelocytic leukemia, pre-B cell leukemia, lymphoma, mantle cell lymphoma, pancreatic cancer, prostate cancer, head and neck cancer, ovarian cancer, melanoma, giloma, liver cancer, renal cancer, colorectal cancer, rhabdomyosarcoma, tongue cancer, stomach cancer, multiple myeloma, bladder cancer, thyroid cancer, epidermoid carcinoma, NSC lung cancer, or large cell lung cancer.

In certain embodiments, the proliferative disease is leukemia, adult T-cell leukemia, promyelocytic leukemia, pre-B cell leukemia, lymphoma, mantle cell lymphoma, breast cancer, head and neck cancer, ovarian cancer, colorectal cancer, tongue cancer, multiple myeloma, or large cell lung cancer.

In certain embodiments, the subject to be treated with one of the methods provided herein has not been treated with anticancer therapy for the proliferative disease to be treated prior to the administration of a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In certain embodiments, the subject to be treated with one of the methods provided herein has been treated with anticancer therapy for the proliferative disease to be treated prior to the administration of a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In certain embodiments, the subject to be treated with one of the methods provided herein has developed drug resistance to the anticancer therapy.

In certain embodiments, provided herein is a method for treating a subject who has undergone surgery in an attempt to treat the disease or condition at issue, as well as the one who have not. Because the subjects with cancer have heterogeneous clinical manifestations and varying clinical outcomes, the treatment given to a particular subject may vary, depending on his/her prognosis. The skilled clinician will be able to readily determine without undue experimentation, specific secondary agents, types of surgery, and types of non-drug based standard therapy that can be effectively used to treat an individual subject with cancer.

The methods provided herein encompass treating a subject regardless of patient's age, although some diseases or disorders are more common in certain age groups.

Depending on the disease to be treated and the subject's condition, a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. A compound provided herein, e.g., an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, may be formulated, alone or together, in suitable dosage unit with pharmaceutically acceptable excipients, carriers, adjuvants and vehicles, appropriate for each route of administration.

In one embodiment, a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, is administered orally. In another embodiment, a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, is administered parenterally. In yet another embodiment, a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, is administered intravenously. In yet another embodiment, a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, is administered intramuscularly. In yet another embodiment, a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, is administered subcutaneously. In still another embodiment, a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, is administered topically.

A compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof, can be delivered as a single dose such as, e.g., a single bolus injection, or oral tablets or pills; or over time such as, e.g., continuous infusion over time or divided bolus doses over time. The compound provided herein can be administered repetitively if necessary, for example, until the patient experiences stable disease or regression, or until the patient experiences disease progression or unacceptable toxicity. Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

A compound provided herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, can be administered once daily (QD), or divided into multiple daily doses such as twice daily (BID), and three times daily (TID). In addition, the administration can be continuous, i.e., every day, or intermittently. The term "intermittent" or "intermittently" as used herein is intended to mean stopping and starting at either regular or irregular intervals. For example, intermittent administration of a compound provided herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, is administration for one to six days per week, administration in cycles (e.g., daily administration for two to eight consecutive weeks, then a rest period with no administration for up to one week), or administration on alternate days.

In certain embodiments, a compound provided herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, is cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

In one embodiment, provided herein is a method for inducing the production of myelin basic protein in a cell, comprising contacting the cell with a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof.

In another embodiment, provided herein is a method for inhibiting a pro-inflammatory cytokine in a cell, comprising contacting the cell with a compound provided herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof.

In yet another embodiment, provided herein is a method for providing neuroprotection to a subject, comprising administering to the subject a compound provided herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof.

A compound provided herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof, can also be combined or used in combination with other therapeutic agents useful in the treatment and/or prevention of a disease described herein. In certain embodiments, the other therapeutic agent is one that prevents lymphocyte extravasation. In certain embodiments, the other therapeutic agent is one that enhances methylation.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

The route of administration of a compound provided herein, e.g., a compound of Formula I, including an enantiomer, a mixture of enantiomers, or a mixture of diastereomers thereof; or a pharmaceutically acceptable salt, solvate, or prodrug thereof, is independent of the route of administration of a second therapy. In one embodiment, a compound provided herein, e.g., a compound of Formula I, including an enantiomer, a mixture of enantiomers, or a mixture of diastereomers thereof; or a pharmaceutically acceptable salt, solvate, or prodrug thereof, is administered orally. In another embodiment, a compound provided herein, e.g., a compound of Formula I, including an enantiomer, a mixture of enantiomers, or a mixture of diastereomers thereof; or a pharmaceutically acceptable salt, solvate, or prodrug thereof, is administered intravenously. Thus, in accordance with these embodiments, a compound provided herein, e.g., a compound of Formula I, including an enantiomer, a mixture of enantiomers, or a mixture of diastereomers thereof; or a pharmaceutically acceptable salt, solvate, or prodrug thereof, is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, a compound provided herein, e.g., a compound of Formula I, including an enantiomer, a mixture of enantiomers, or a mixture of diastereomers thereof; or a pharmaceutically acceptable salt, solvate, or prodrug thereof, and a second therapy are administered by the same mode of administration, orally or by IV. In another embodiment, a compound provided herein, e.g., a compound of Formula I, including an enantiomer, a mixture of enantiomers, or a mixture of diastereomers thereof; or a pharmaceutically acceptable salt, solvate, or prodrug thereof, is administered by one mode of administration, e.g., by IV, whereas the second agent (an anticancer agent) is administered by another mode of administration, e.g., orally.

In certain embodiments, each method provided herein may independently, further comprise the step of administering a second therapeutic agent.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

In certain embodiments, provided herein also are kits which, when used by the medical practitioner, can simplify the administration of appropriate amounts of active ingredients to a subject. In certain embodiments, the kit provided herein includes a container and a dosage form of a compound provided herein, including a single enantiomer or a mixture of diastereomers thereof; or a pharmaceutically acceptable salt, solvate, or prodrug thereof.

In certain embodiments, the kit includes a container comprising a dosage form of the compound provided herein, including a single enantiomer or a mixture of diastereomers thereof; or a pharmaceutically acceptable salt, solvate, or prodrug thereof, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

In certain embodiments, provided herein is a method of reducing the secretion of a pro-inflammatory cytokine in a cell, comprising the step of contacting the cell with an effective amount of a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof. In certain embodiments, the pro-inflammatory cytokine is tumor necrosis factor-alpha (TNF-α). In certain embodiments, the cell is a human cell.

In certain embodiments, provided herein is a method of protecting an oligodendrocyte against apoptosis induced by a pro-inflammatory cytokine, comprising the step of contacting the oligodendrocyte with an effective amount of a compound provided herein, e.g., a compound of Formula I, including an enantiomer, a mixture of enantiomers, a mixture of two or more diastereomers, a tautomer, a mixture of two or more tautomers, or an isotopic variant thereof; or a pharmaceutically acceptable salt, solvate, hydrate, or prodrug thereof. In certain embodiments, the pro-inflammatory cytokine is tumor necrosis factor-alpha (TNF-α). In certain embodiments, the oligodendrocyte is a human oligodendrocyte.

In certain embodiments, provided herein is a method of inducing the production of myelin basic protein in a cell, comprising the step of contacting the cell with an effective amount of a compound provided herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof. In certain embodiments, the cell is a human cell.

In certain embodiments, provided herein is a method of inhibiting the growth of a cell, comprising the step of contacting the cell with with an effective amount of a compound provided herein, e.g., a compound of Formula I, including an enantiomer, a mixture of enantiomers, a mixture of two or more diastereomers, a tautomer, a mixture of two or more tautomers, or an isotopic variant thereof, or a pharmaceutically acceptable salt, solvate, hydrate, or prodrug thereof.

In certain embodiment, the cell is a tumor cell. In certain embodiment, the cell is a mammalian tumor cell. In certain embodiment, the cell is a human tumor cell. In certain embodiment, the cell is a cancerous cell. In certain embodiment, the cell is a mammalian cancerous cell. In certain embodiment, the cell is a human cancerous cell. In certain embodiment, the cancerous cell is a metastatic cancerous cell. In certain embodiment, the cancerous cell is a metastatic microbial cell. In certain embodiment, the cancerous cell is a metastatic bacterial cell. In certain embodiment, the cancerous cell is a metastatic fungal cell.

In certain embodiment, the cell is a hematologic malignancy cell. In certain embodiment, the cell is a leukemia cell. In certain embodiments, the cell is a relapsed leukemia cell. In certain embodiments, the cell is a refractory leukemia cell. In certain embodiments, the cell is a drug-resistant leukemia cell. In certain embodiments, the cell is a multidrug-resistant leukemia cell. In certain embodiments, the cell is a Bcr-Abl kinase inhibitor-resistant leukemia cell. In certain embodiments, the cell is an imatinib-resistant leukemia cell. In certain embodiments, the cell is a dasatinib-resistant leukemia cell. In certain embodiments, the cell is a nilatinib-resistant leukemia cell. In certain embodiments, the cell is a bosutinib-resistant leukemia cell. In certain embodiments, the cell is a cytarabine-resistant leukemia cell.

In certain embodiment, the cell is a leukemia stem cell. In certain embodiments, the cell is a relapsed leukemia stem cell. In certain embodiments, the cell is a refractory leukemia stem cell. In certain embodiments, the cell is a drug-resistant leukemia stem cell. In certain embodiments, the cell is a multidrug-resistant leukemia stem cell. In certain embodiments, the cell is a Bcr-Abl kinase inhibitor-resistant leukemia stem cell. In certain embodiments, the cell is an imatinib-resistant leukemia stem cell. In certain embodiments, the cell is a dasatinib-resistant leukemia stem cell. In certain embodiments, the cell is a nilatinib-resistant leukemia stem cell. In certain embodiments, the cell is a bosutinib-resistant leukemia stem cell. In certain embodiments, the cell is a cytarabine-resistant leukemia stem cell.

In certain embodiment, the cell is an acute leukemia cell. In certain embodiments, the cell is a relapsed acute leukemia cell. In certain embodiments, the cell is a refractory acute leukemia cell. In certain embodiments, the cell is a drug-resistant acute leukemia cell. In certain embodiments, the cell is a multidrug-resistant acute leukemia cell. In certain embodiments, the cell is a Bcr-Abl kinase inhibitor-resistant acute leukemia cell. In certain embodiments, the cell is an imatinib-resistant acute leukemia cell. In certain embodiments, the cell is a dasatinib-resistant acute leukemia cell. In certain embodiments, the cell is a nilatinib-resistant acute leukemia cell. In certain embodiments, the cell is a bosutinib-resistant acute leukemia cell. In certain embodiments, the cell is a cytarabine-resistant acute leukemia cell.

In certain embodiments, the cell is an ALL cell. In certain embodiments, the cell is a relapsed ALL cell. In certain embodiments, the cell is a refractory ALL cell. In certain embodiments, the cell is a drug-resistant ALL cell. In certain embodiments, the cell is a multidrug-resistant ALL cell. In certain embodiments, the cell is a Bcr-Abl kinase inhibitor-resistant ALL cell. In certain embodiments, the cell is an imatinib-resistant ALL cell. In certain embodiments, the cell is a dasatinib-resistant ALL cell. In certain embodiments, the cell is a nilatinib-resistant ALL cell. In certain embodiments, the cell is a bosutinib-resistant ALL cell. In certain embodiments, the cell is a cytarabine-resistant ALL cell.

In certain embodiments, the cell is an AML cell. In certain embodiments, the cell is a relapsed AML cell. In certain embodiments, the cell is a refractory AML cell. In certain embodiments, the cell is a drug-resistant AML cell. In certain embodiments, the cell is a multidrug-resistant AML cell. In certain embodiments, the cell is a Bcr-Abl kinase inhibitor-resistant AML cell. In certain embodiments, the cell is an imatinib-resistant AML cell. In certain embodiments, the cell is a dasatinib-resistant AML cell. In certain embodiments, the cell is a nilatinib-resistant AML cell. In certain embodiments, the cell is a bosutinib-resistant AML cell. In certain embodiments, the cell is a cytarabine-resistant AML cell.

In certain embodiment, the cell is a chronic leukemia cell. In certain embodiments, the cell is a relapsed chronic leukemia cell. In certain embodiments, the cell is a refractory chronic leukemia cell. In certain embodiments, the cell is a drug-resistant chronic leukemia cell. In certain embodiments, the cell is a multidrug-resistant chronic leukemia cell. In certain embodiments, the cell is a Bcr-Abl kinase inhibitor-resistant chronic leukemia cell. In certain embodiments, the cell is an imatinib-resistant chronic leukemia cell. In certain embodiments, the cell is a dasatinib-resistant chronic leukemia cell. In certain embodiments, the cell is a nilatinib-resistant chronic leukemia cell. In certain embodiments, the cell is a bosutinib-resistant chronic leukemia cell. In certain embodiments, the cell is a cytarabine-resistant chronic leukemia cell.

In certain embodiments, the cell is a CLL cell. In certain embodiments, the cell is a relapsed CLL cell. In certain embodiments, the cell is a refractory CLL cell. In certain embodiments, the cell is a drug-resistant CLL cell. In certain embodiments, the cell is a multidrug-resistant CLL cell. In certain embodiments, the cell is a Bcr-Abl kinase inhibitor-resistant CLL cell. In certain embodiments, the cell is an imatinib-resistant CLL cell. In certain embodiments, the cell is a dasatinib-resistant CLL cell. In certain embodiments, the cell is a nilatinib-resistant CLL cell. In certain embodiments, the cell is a bosutinib-resistant CLL cell. In certain embodiments, the cell is a cytarabine-resistant CLL cell.

In certain embodiments, the cell is a CML cell. In certain embodiments, the cell is a relapsed CML cell. In certain embodiments, the cell is a refractory CML cell. In certain embodiments, the cell is a drug-resistant CML cell. In certain embodiments, the cell is a multidrug-resistant CML cell. In certain embodiments, the cell is a Bcr-Abl kinase inhibitor-resistant CML cell. In certain embodiments, the cell is an imatinib-resistant CML cell. In certain embodiments, the cell is a dasatinib-resistant CML cell. In certain embodiments, the cell is a nilatinib-resistant CML cell. In certain embodiments, the cell is a bosutinib-resistant CML cell. In certain embodiments, the cell is a cytarabine-resistant CML cell.

In certain embodiments, the cell is Philadelphia positive leukemia cell. In one embodiment, the cell is a Philadelphia positive ALL cell. In another embodiment, the cell is a Philadelphia positive AML cell. In yet another embodiment, the cell is a Philadelphia positive CLL cell. In still another embodiment, the cell is a Philadelphia positive CML cell.

The inhibition of cell growth can be gauged by, e.g., counting the number of cells contacted with a compound of interest, comparing the cell proliferation with otherwise identical cells not contacted with the compound, or determining the size of the tumor that encompasses the cells. The number of cells, as well as the size of the cells, can be readily assessed using any method known in the art (e.g., trypan blue exclusion and cell counting, measuring incorporation of $^3$H-thymidine into nascent DNA in a cell).

In certain embodiment, the effective amount of the compound provided herein ranges from about 1 pM to about 1 mM, from about 10 pM to about 1 µM, from about 100 pM to about 2 µM, or from about 1 nM to about 1 µM.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society, the Journal of Medicinal Chemistry, or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); Hz (Hertz); MHz (megahertz); mmol (millimoles); hr or hrs (hours); min (minutes); MS (mass spectrometry); ESI (electrospray ionization); TLC (thin layer chromatography); HPLC (high pressure liquid chromatography); and CDCl$_3$ (deuterated chloroform).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

Example C1

Preparation of 6-cyclohexyl-4-methylpyridine-2(1H)-thione A1

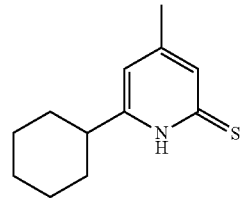

A 100 mL round bottom flask was charged with 6-cyclohexyl-4-methyl-1H-pyridin-2-one (0.330 gram, 1.73 mmol) and 2,4-bis(4-methoxyphenyl)-1,3,2,4-dithiadiphosphetane-2,4-disulfide (Lawesson's reagent, 1.00 gram, 2.48 mmol). Dry benzene (20 mL) was added to the flask, and the reaction mixture was stirred for 1 day at 80° C. The mixture was then cooled to room temperature and concentrated under vacuum. The crude product was purified by silica gel chromatography using hexanes/ethyl acetate (4:1), followed by trituration with hexanes then ether to afford compound A1 (0.183 g, 51% yield). MS (M+1): 208; $^1$H NMR (CDCl$_3$) δ 12.09 (bs, 1H), 7.23 (s, 1H), 6.33 (s, 1H), 2.63 (m, 1H), 2.20 (s, 3H), 1.96 (m, 2H), 1.86 (m, 2H), 1.76 (m, 1H), 1.39 (m, 4H), 1.25 (m, 1H).

Example C2

Preparation of 4-methyl-6-(2,4,4-trimethylpentyl)pyridine-2(1H)-thione A2

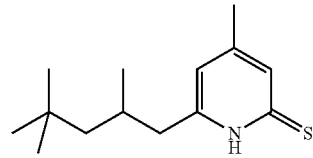

A 100 mL round bottom flask was charged with piroctone olamine (1.00 gram, 3.35 mmol) and 2,4-bis(4-methoxyphenyl)-1,3,2,4-dithiadiphosphetane-2,4-disulfide (Lawesson's reagent, 1.76 grams, 4.36 mmol). Dry benzene (30 mL) was added to the flask, and the reaction mixture was stirred for 1 day at 80° C. The mixture was then cooled to room temperature and concentrated under vacuum. The crude product was triturated with hexanes/ether (1:1) then purified by silica gel chromatography using hexanes/ethyl acetate (4:1) to afford compound A2 (0.165 g, 21% yield). MS (M+1): 238. $^1$H NMR (CDCl$_3$) δ 12.06 (bs, 1H), 7.24 (s, 1H), 6.31 (s, 1H), 2.57 (dd, 1H, J=0.013, 0.028), 2.43 (dd, 1H, J=0.017, 0.028), 2.21 (s, 3H), 1.90 (m, 1H), 1.26 (dd, 1H, J=0.006, 0.028), 1.14 (dd, 1H, J=0.014, 0.028), 0.96 (d, 3H, J=0.013), 0.87 (s, 9H).

Example C3

Preparation of 6-isopropyl-4-methylpyridine-2(1H)-thione A5

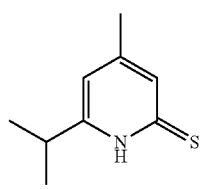

A5

The synthesis of 6-isopropyl-4-methylpyridine-2(1H)-thione A5 is shown in Scheme 1.

Scheme 1

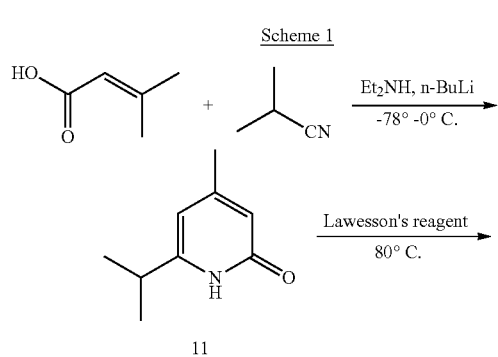

To a solution of diethylamine (160 mg, 2.2 mmol) in tetrahydrofuran (4 mL) at −78° C. was added n-butyl lithium (4.4 mL, 10.98 mmol, 2.5 M in hexane) under nitrogen. After the solution was stirred at 0° C. for 30 min, 3-methylbut-2-enoic acid (500 mg, 4.99 mmol) in tetrahydrofuran (4 mL) was added at −78° C. The mixture was stirred at 0° C. for 30 min, followed by addition of isobutyronitrile (344.3 mg, 4.99 mmol) in tetrahydrofuran (4 mL) at −78° C. After gradually warmed to room temperature, the reaction mixture was stirred for 24 hrs. TLC (EtOAc, UV) showed some of 3-methylbut-2-enoic acid was remained and new spots were present. The reaction was poured into water (10 mL) and extracted with dichloromethane (30 mL×2). The combined organic layers were washed with water, brine, dried over sodium sulfate, filtered, and concentrated to give a crude product, which was triturated with ethyl acetate (3 mL) to give 6-isopropyl-4-methylpyridin-2(1H)-one (11) (96 mg). The filtrate was concentrated and purified by preparative TLC (EtOAc) to give an additional 53 mg of 6-isopropyl-4-methylpyridin-2(1H)-one (11). $^1$H NMR (400 MHz, DMSO-$d_6$) δ 11.27 (s, 1H), 5.94 (s, 1H), 5.85 (s, 1H), 2.73-2.66 (m, 1H), 2.08 (s, 3H), 1.16 (s, 3H), 1.14 (s, 3H).

To a solution of 6-isopropyl-4-methylpyridin-2(1H)-one (11) (96 mg, 0.635 mmol) in toluene (15 mL) at room temperature was added Lawesson's reagent (383.9 mg, 0.952 mmol). The suspension was heated at 80° C. for 16 hrs. TLC (EtOAc, UV) showed most of 6-isopropyl-4-methylpyridin-2(1H)-one (11) was consumed and some spots were present. The solvent was removed and the residue was purified by silica-gel column chromatography eluting with petroleum ether/ethyl acetate from 5% to 18% to give a crude product, which was triturated with ethyl acetate (5 mL) to give 6-isopropyl-4-methylpyridine-2(1H)-thione (A5) (67 mg, yield: 63.2%). MS (ESI) m/z: 168.0 [M+H]+; $^1$H NMR (400 MHz, DMSO-$d_6$) δ 13.06 (br s, 1H), 6.98 (s, 1H), 6.49 (s, 1H), 3.01-2.94 (m, 1H), 2.14 (s, 3H), 1.19 (s, 3H), 1.17 (s, 3H).

Example C4

Preparation of 4-isopropyl-6-methylpyridine-2(1H)-thione A6

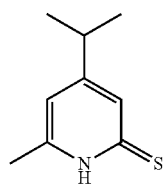

A6

The synthesis of 4-isopropyl-6-methylpyridine-2(1H)-thione A6 is shown in Scheme 2.

Scheme 2

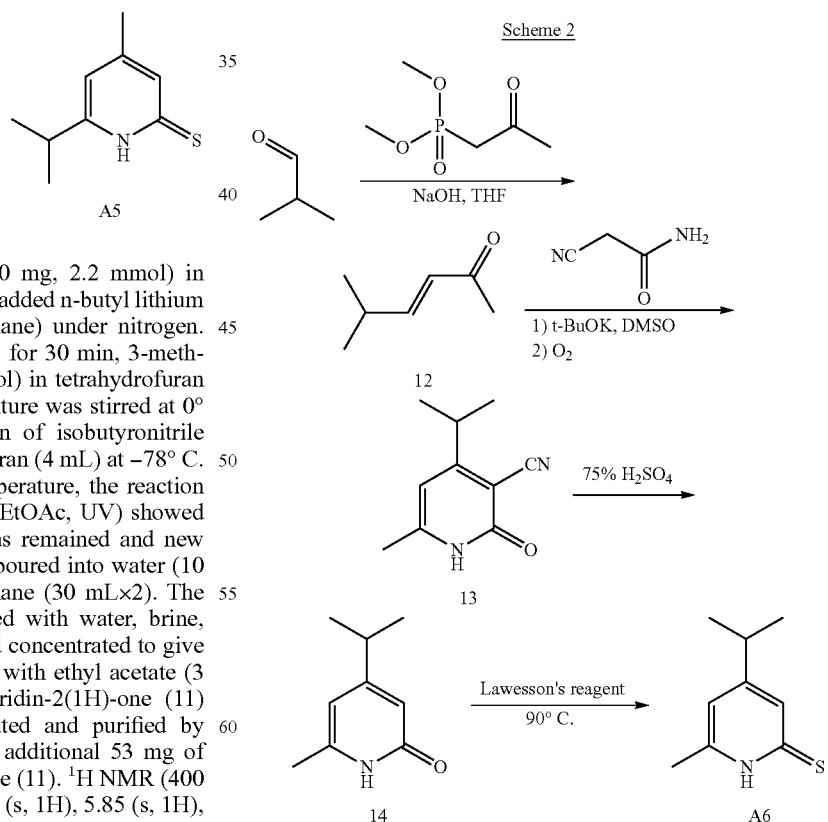

To tetrahydrofuran (20 mL) was added 5M sodium hydroxide (10.5 mL, 52.5 mmol) at 5° C. After the solution was stirred at 5° C. for 15 min, isobutyraldehyde (3.6 g, 50 mmol) in tetrahydrofuran (15 mL) was added dropwise at 5° C. The reaction mixture was stirred at 5° C. for 1 hr. The reaction mixture was diluted with tert-butyl methyl ether (150 mL), washed with brine (100 mL), dried over sodium sulfate, filtered, and concentrated to give (E)-5-methylhex-3-en-2-one (12) (4.7 g, yield: 85%). MS (ESI) m/z: 113.2 [M+H]+; $^1$H NMR (300 MHz, CDCl$_3$) δ 6.76 (dd, J=6.6, 16.2 Hz, 1H), 6.02 (d, J=16.2 Hz, 1H), 2.51-2.43 (m, 1H), 2.24 (s, 3H), 1.07 (d, J=6.6 Hz, 6H).

To a solution of 2-cyanoacetamide (1.00 g, 12 mmol) in dimethyl sulfoxide (20 mL) was added potassium tert-butoxide (1.12 g, 10 mmol) in portions at 15° C. under nitrogen. After the reaction mixture was stirred for 10 min, (E)-5-methylhex-3-en-2-one (12) (1.12 g, 10 mmol) was added dropwise over 5 min. The reaction mixture was stirred at 15° C. for 30 min. Additional potassium tert-butoxide (3.36 g, 30 mmol) was added in portions while the reaction temperature was kept under 30° C. After stirred at 15° C. under oxygen atmosphere overnight, the reaction mixture was poured into ice-cold water (100 mL) with stirring, acidified with 4 N hydrochloride acid to pH=3, filtered, and washed with cold water (10 mL×3). The solid was dried under vacuum to give 4-isopropyl-6-methyl-2-oxo-1,2-dihydropyridine-3-carbonitrile (13) (560 mg, yield: 32%). MS (ESI) m/z: 177.1 [M+H]$^+$; $^1$H NMR (300 MHz, DMSO-d$_6$) δ 12.36 (s, 1H), 6.29 (s, 1H), 3.01 (heptet, J=6.9 Hz, 1H), 2.25 (s, 3H), 1.18 (d, J=6.9 Hz, 6H).

A mixture of 4-isopropyl-6-methyl-2-oxo-1,2-dihydropyridine-3-carbonitrile (13) (468 mg, 2.7 mmol) in 75% sulfuric acid (10 mL) was stirred at 140° C. for 6 hrs. The reaction mixture was then cooled to 0° C., neutralized with 50% sodium hydroxide to pH=3, and extracted with dichloromethane/methanol (10:1; 100 mL×3). The combined organic layers were dried over sodium sulfate, filtered, concentrated, and purified with silica gel column (dichloromethane to dichloromethane/methanol (15:1) to give 4-isopropyl-6-methylpyridin-2(1H)-one (14) (339 mg, 88%). MS (ESI) m/z: 152.1 [M+H]+; $^1$H NMR (300 MHz, DMSO-d$_6$) δ 11.31 (s, 1H), 5.91 (s, 2H), 2.60 (heptet, J=6.9 Hz, 1H), 2.12 (s, 3H), 1.10 (d, J=6.9 Hz, 6H).

To a solution of 4-isopropyl-6-methylpyridin-2(1H)-one (14) (375 mg, 2.5 mmol) in toluene (18 mL) was added Lawesson's Reagent (2.1 g, 5 mmol) at room temperature. The suspension was heated at 90° C. for 2 hrs. The solvent was removed and the residue was purified by silica gel column (dichloromethane to dichloromethane/ethyl acetate (3:1) to give a crude product, which was purified with preparative TLC (dichloromethane/methanol (25:1)) to give 4-isopropyl-6-methylpyridine-2(1H)-thione (A6) (290 mg, 70%). MS (ESI) m/z: 168.0 [M+H]$^+$; $^1$H NMR (400 MHz, DMSO-d$_6$) δ 13.13 (s, 1H), 6.96 (s, 1H), 6.53 (s, 1H), 2.67 (heptet, J=6.8 Hz, 1H), 2.28 (s, 3H), 1.12 (d, J=6.8 Hz, 6H).

Example C5

Preparation of 6-cyclopropyl-4-methylpyridine-2(1H)-thione A7

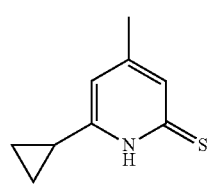

A7

The synthesis of 6-cyclopropyl-4-methylpyridine-2(1H)-thione A7 is shown in Scheme 3.

Scheme 3

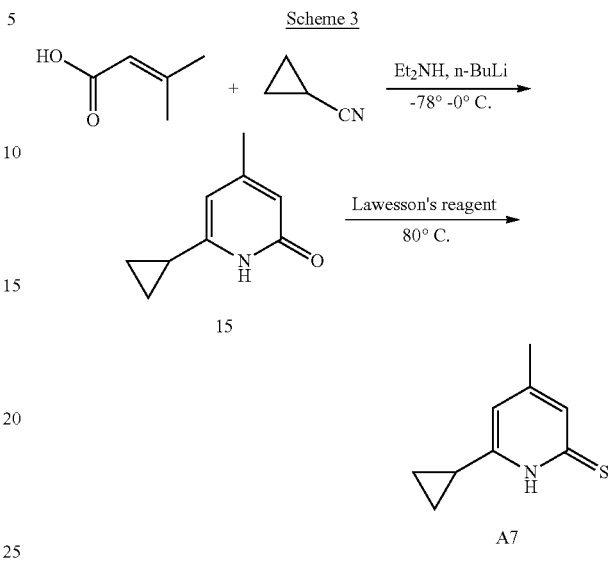

To a solution of diethylamine (321 mg, 4.4 mmol) in tetrahydrofuran (8 mL) at −78° C. was added n-butyl lithium (8.8 mL, 22 mmol, 2.5 M in hexane) under nitrogen. After the solution was stirred at 0° C. for 30 min, 3-methylbut-2-enoic acid (1.0 g, 10 mmol) in tetrahydrofuran (8 mL) was added at −78° C. The mixture was stirred at 0° C. for 30 min, followed by addition of cyclopropanecarbonitrile (602 mg, 10 mmol) in tetrahydrofuran (8 mL) at −78° C. After gradually warmed to room temperature, the reaction mixture was stirred for 24 hrs. TLC (EtOAc, UV) showed some of 3-methylbut-2-enoic acid was remained and new spots were present. The reaction mixture was poured into water (20 mL) and extracted with dichloromethane (40 mL×2). The combined organic layers were washed with water, brine, dried over sodium sulfate, filtered, and concentrated to give a crude product, which was triturated with ethyl acetate (3 mL) to give 6-cyclopropyl-4-methylpyridin-2(1H)-one (15) (316 mg, yield: 21.2%). MS (ESI) m/z: 150.1 [M+H]$^+$.

To a solution of 6-cyclopropyl-4-methylpyridin-2(1H)-one (15) (182 mg, 1.21 mmol) in toluene (40 mL) at room temperature was added Lawesson's Reagent (975 mg, 2.42 mmol). The suspension was heated at 80° C. for 16 hrs. TLC (EtOAc, UV) showed most of 6-cyclopropyl-4-methylpyridin-2(1H)-one (15) was consumed and some spots were present. The solvent was removed and the residue was purified by silica-gel column chromatography eluting with petroleum ether/ethyl acetate from 10 to 20% to give a crude product, which was triturated with ethyl acetate (5 mL) to give 6-cyclopropyl-4-methylpyridine-2(1H)-thione (A7) (43.4 mg, yield: 21.7%). MS (ESI) m/z: 166.1 [M+H]$^+$; $^1$H NMR (400 MHz, DMSO-d$_6$) δ 13.29 (br s, 1H), 6.91 (s, 1H), 6.14 (s, 1H), 2.11-2.04 (m, 1H), 2.09 (s, 3H), 1.07-1.02 (m, 2H), 0.84-0.80 (m, 2H).

Example B1

Protection of Oligodendrocytes from Cuprizone Demyelination

MO3-13 cells were plated onto 6 cm cell culture dishes and grown in DMEM containing 5% FBS. Cells were grown to 75% confluence, then serum containing DMEM medium was replaced with FBS free DMEM. Cells were grown for 48 hours under serum-deprived conditions. Cuprizone (CPZ) (final concentration of 50 µM in 100% ethanol) was added to selected dishes with and without a test article (the control compound and compounds A1 to A3 were each at 5 µM in DMSO) and incubated for 48 hours. Analysis was performed using an inverted Zeiss microscope equipped with phase contrast optics. Images were captured using Volocity software. Results are shown in FIG. 1

Example B2

Figure 2:
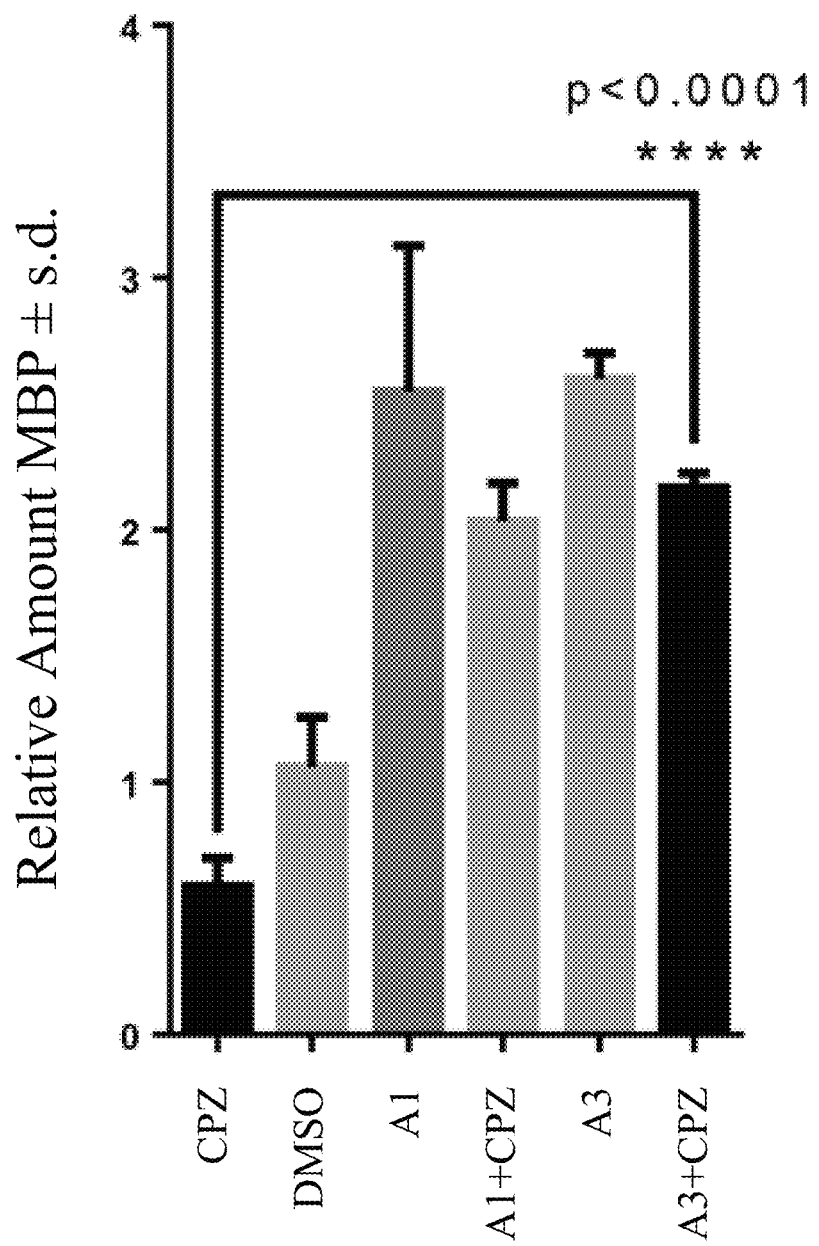
FIG. 2 shows the induction of myelin basic protein (MBP) production with compounds A1 and A3 on human oligodendrocytes (MO3-13) in the presence or absence of cuprizone.
Figure 3:
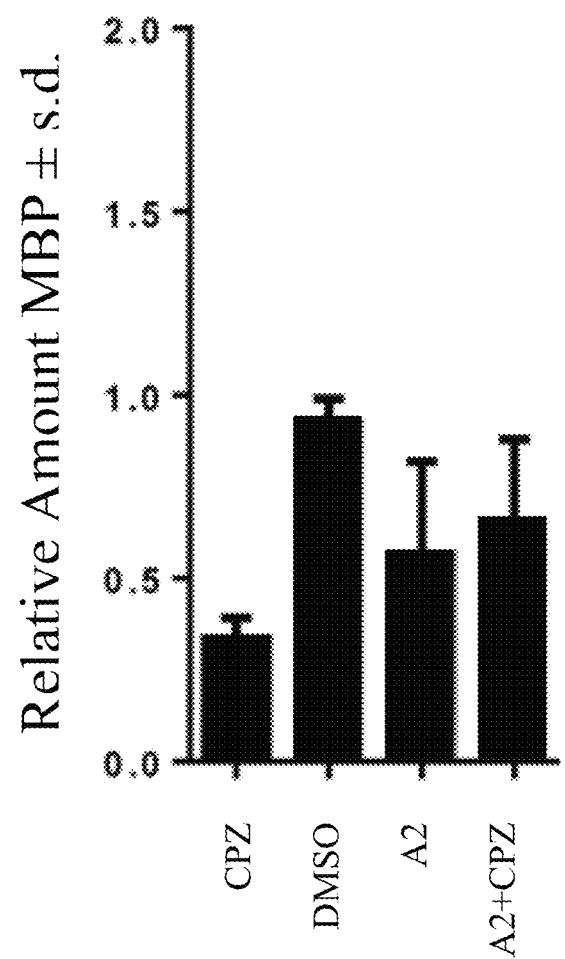
FIG. 3 shows the induction of myelin basic protein (MBP) production with compound A2 on human oligodendrocytes (MO3-13) in the presence or absence of cuprizone.

Induction of Myelin Basic Protein (MBP) Production and Protection of Oligodendrocytes from Cuprizone Demyelination Whole cell extracts of MO3-13 cells were prepared using 6 M urea. An aliquot of 100 µL was removed and diluted with an equal volume of 6 M urea. A 5 µL aliquot was removed and quantitated for protein levels. Total protein concentrations were determined using the BioRad protein assay method at 595 nm. Total protein in the whole cell extracts was determined and a ratio of recovered protein was used to calculate the relative amount of MBP in the whole cell extracts. Whole cell extracts were diluted to 0.1 mg/mL. Extracts containing 2.5 µg of protein were applied onto nitrocellulose membrane in a slot blotter using a vacuum method to draw the sample onto the membrane. The non-protein sites on the membrane were blocked with 2% ECL blocking reagent diluted in PBS-Tween20. Primary anti-Bovine MBP was diluted in the same block solution at 300×. The primary antibody was incubated one hour at room temperature with gentle shaking. The blot was developed using enhanced ECL (GE Healthcare) method. Image of bound antibody were captured using Image Lab software driving a Bio-Rad ChemiDoc XRS+ image capture system. The data was graphically represented using Graph Pad Prism software. The data revealed that treatment of MO3-13 cells with cuprizone resulted in reduced anti-MBP antibody binding as compared with non-treated DMSO vehicle cells. Cells treated with compound A1 or A3 with and without cuprizone revealed elevated relative MBP binding. This was significantly increased above vehicle control, p<0.0001(****). Results are shown in FIG. 2. Similarly, cells treated with compound A2 with and without cuprizone revealed elevated relative MBP binding.

Example B3

Protection of Animals from Cuprizone Demyelination

The ability of compound A1 to effect the demyelination process was evaluated in a cuprizone model of demyelination in mice. Thirty-six male C57/B6 mice aged 7-8 weeks were acclimated for 1 week prior to study commencement and housed 2 mice per cage. Mice were divided into four groups as shown in Table 1. Mice in Group 1 received control chow without cuprizone, and all other mice were fed mouse diet containing 0.2% cuprizone for 5 weeks. Food was changed every other day, body and food weights were obtained daily. All cuprizone and control food was stored in vacuum containers and stored frozen until use.

TABLE 1

| Group No. | Number of Animals | Cuprizone Treatment | Treatment | Schedule |
|---|---|---|---|---|
| 1 | 6 males | No cuprizone | None | NA |
| 2 | 10 males | 5 weeks | Vehicle IP | Weeks 1-5 QD |
| 3 | 10 males | 5 weeks | Cmpd A1 50 mg/kg | Weeks 1-5 QD |
| 4 | 10 males | 5 weeks | Cmpd A1 100 mg/kg | Weeks 1-5 QD |

Dosing solutions were prepared fresh on each day of dosing. Compound A1 was first dissolved in DMSO in a volume of 10% of the final volume, followed by addition of solutol HS-15 in a volume of 10% of the final volume and a solution of 10% hydroxypropyl-β-cyclodextrin in a volume of 80% of the final volume. Unless otherwise noted, all test articles were administered in a volume of 0.1 mL/10 g body weight.

During this process, mice received either vehicle or compound A1 at 50 mg/kg or 100 mg/kg via intraperitoneal injection daily. At the end of 5 weeks, the mice were sacrificed and the brain histology of each group compared to controls that had not received cuprizone. Statistical differences between treatment groups were determined using Mann-Whitney Rank Sum or ANOVA tests with a critical value of 0.05.

All animals were weighed every day in order to assess possible differences in animal weight among treatment groups as an indication of possible toxicity resulting from the treatments. Animals with a weight loss of more than 20% of their starting weight were euthanized. Mice with weight loss of more than 15% of their starting weight were not treated again until weight loss recovered to less than 5% of their starting weight. Between Days 20 and 24, nine often mice in the compound A1 (100 mg/kg) treatment group suddenly started to lose weight and die, despite discontinuation of the compound A1 dosing. One animal in the cuprizone/vehicle group was also euthanized on Day 20 due to poor condition and weight loss. All remaining mice survived until the end of the study.

The control group (no cuprizone) gained an average of 11.3% of their starting weight during the study. The vehicle control group (receiving cuprizone food) lost an average of 9.3% of their starting weight during the study. Similarly, the group receiving cuprizone food and compound A1 at 50 mg/kg lost an average of 10.6% of their starting weight during the study. In both groups, the bulk of the weight loss occurred during the first week of the study, and weights were relatively stable from Day 7 to Day 35. The group receiving cuprizone food and compound A1 at 100 mg/kg showed a similar pattern until Day 20, when there was a period of weight loss (and animal deaths). The sole surviving animal in this group exhibit 15.7% weight loss when treatment with compound A1 was discontinued on Day 20, and 13.1% loss (of starting weight) on Day 35 (cuprizone food was continued until Day 35).

Additional analysis of the weight changes observed was conducted by calculating the area under the curve (AUC) for each mouse and comparing the AUC values for different treatment groups using a one-way ANOVA test. The results of this test showed that there were statistically significant differences between the control (no cuprizone) group and the groups that received cuprizone containing food (p<0.001 in all cases), but no statistically significant differences were seen between the different treatment groups.

Evaluation of the myelin content of the brains was focused on three areas—the rostral corpus callosum, the dorsal corpus callosum and the cerebellum. The extent of demyelination in both sagittal sections was determined by a board certified veterinary pathologist blinded to animal treatment. Percent demyelination was scored as follows: demyelination ranging from 0 to 10% of the total anatomical structure was scored as 0; demyelination ranging from 11 to 30% of the total anatomical structure was scored as 1; demyelination ranging from 31 to 60% of the total anatomical structure was scored as 2; demyelination ranging from 61 to 90% of the total anatomical structure was scored as 3; and demyelination ranging from 91 to 100% of the total anatomical structure was scored as 4. The extent of MBP staining intensity was based on a 1-4 scale, where 4 was the highest level of staining seen (100%).

The mean rostral corpus callosum myelination score for the control group was 3.7. In the vehicle treated group receiving cuprizone chow, the mean rostral corpus callosum myelination score was 1.8. In the group receiving cuprizone chow and compound A1 at 50 mg/kg, the mean rostral corpus callosum myelination score was 2.1. Additional analysis of the rostral corpus callosum myelination scores was conducted using an ANOVA test. The results of this test showed that there were statistically significant differences between the control (no cuprizone) group and the groups that received cuprizone containing food ($p=0.0008$ in the vehicle group, $p<0.0001$ in the compound A1, 50 mg/kg group), but no statistically significant differences were seen between the different treatment groups.

The mean caudal corpus callosum myelination score for the control group was 3.7. In the vehicle treated group receiving cuprizone chow, the mean caudal corpus callosum myelination score was 1.2. In the group receiving cuprizone chow and compound A1 at 50 mg/kg, the mean caudal corpus callosum myelination score was 2.1. Additional analysis of the caudal corpus callosum myelination scores was conducted using an ANOVA test. The results of this test showed that there were statistically significant differences between the control (no cuprizone) group and the groups that received cuprizone containing food ($p<0.0001$ in the vehicle group, $p=0.0003$ in the compound A1, 50 mg/kg group), and statistically significant differences were seen between the vehicle control group and the group treated with compound A1 at 50 mg/kg ($p=0.0012$).

The mean cerebellar myelination score for the control group was 4. In the vehicle treated group receiving cuprizone chow, the mean cerebellar myelination score was 3. In the group receiving cuprizone chow and compound A1 at 50 mg/kg, the mean rostral corpus callosum myelination score was 3.2. Additional analysis of the cerebellar myelination scores was conducted using an ANOVA test. The results of this test showed that there were no statistically significant differences between the control (no cuprizone) group and the groups that received cuprizone containing food or between the different cuprizone-exposed treatment groups.

In addition, immunohistochemistry was performed for myelin basic protein (MBP), and slides were analyzed for the intensity of MBP staining in the same regions. The mean rostral corpus callosum MBP staining score for the control groups was 4. In the vehicle treated group receiving cuprizone chow, the mean rostral corpus callosum m MBP staining score was 2.9. In the group receiving cuprizone chow and compound A1 at 50 mg/kg, the mean rostral corpus callosum MBP staining score was 3.2. Additional analysis of the rostral corpus callosum MBP staining was conducted using an ANOVA test. The results of this test showed that there were statistically significant differences between the control (no cuprizone) group and the groups that received cuprizone containing food ($p=0.0125$ in the vehicle group, $p=0.0004$ in the compound A1 50 mg/kg group), but no statistically significant differences were seen between the different treatment groups.

The mean caudal corpus callosum MBP staining score for the control groups was 4. In the vehicle treated group receiving cuprizone chow, the mean caudal corpus callosum m MBP staining score was 2.3. In the group receiving cuprizone chow and compound A1 at 50 mg/kg, the mean caudal corpus callosum MBP staining score was 3.1. Additional analysis of the caudal corpus callosum MBP staining was conducted using an ANOVA test. The results of this test showed that there were statistically significant differences between the control (no cuprizone) group and the groups that received cuprizone containing food ($p<0.0001$ in the vehicle group, $p=0.0018$ in the compound A1 50 mg/kg group), and statistically significant differences were seen between the vehicle control group and the group treated with compound A1 at 50 mg/kg ($p=0.0064$).

The mean cerebellum MBP staining score for the control groups was 4. In the vehicle treated group receiving cuprizone chow, the mean cerebellum m MBP staining score was 3.5. In the group receiving cuprizone chow and compound A1 at 50 mg/kg, the mean cerebellum MBP staining score was 3.8. Additional analysis of the cerebellum MBP staining was conducted using an ANOVA test. The results of this test showed that no statistically significant differences were seen between the different groups In conclusion, the group treated with compound A1 at 50 mg/kg daily showed no evidence of toxicity beyond that seen in the vehicle group associated with the cuprizone treatment. Statistically significant demyelination was seen in animals treated with cuprizone relative to untreated animals in the rostral and caudal corpus callosum, but not in the cerebellum. There were no statistically significant differences between the demyelination seen in the vehicle treated and compound A1 treated groups in the rostral corpus callosum, but the dorsal corpus callosum in mice receiving compound A1 showed significantly less demyelination than the mice receiving vehicle ($p=0.0012$). Statistically significant differences in MBP expression were seen in animals treated with cuprizone relative to untreated animals in the rostral and caudal corpus callosum, but not in the cerebellum. There were no statistically significant differences between MBP expression seen in the vehicle treated and compound A1 treated groups in the rostral corpus callosum, but the dorsal corpus callosum in mice receiving compound A1 showed significantly less demyelination than the mice receiving vehicle ($p=0.0064$).

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A pharmaceutical composition comprising a compound of Formula I:

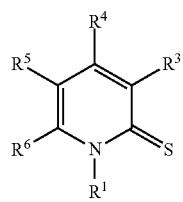

(I)

or an enantiomer, a mixture of enantiomers, a mixture of two or more diastereomers, a tautomer, a mixture of two or more tautomers, or an isotopic variant thereof; or a pharmaceutically acceptable salt, solvate, or hydrate thereof; and a pharmaceutically acceptable excipient;
wherein:

$R^1$ is hydrogen or deuterium;

$R^3$ and $R^5$ are each independently (a) hydrogen, deuterium, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)NR$^{1b}$R$^{1c}$, —C(O)S$R^{1a}$, —C(NR$^{1a}$)NR$^{1b}$R$^{1c}$, —C(S)$R^{1a}$, —C(S)O$R^{1a}$, —C(S)NR$^{1b}$R$^{1c}$, —O$R^{1a}$, —OC(O)$R^{1a}$, —OC(O)O$R^{1a}$, —OC(O)NR$^{1b}$R$^{1c}$, —OC(O)S$R^{1a}$, —OC(=NR$^{1a}$)NR$^{1b}$R$^{1c}$, —OC(S)$R^{1a}$, —OC(S)O$R^{1a}$, —OC(S)NR$^{1b}$R$^{1c}$, —OS(O)$R^{1a}$, —OS(O)$_2$$R^{1a}$, —OS(O)NR$^{1b}$R$^{1c}$, —OS(O)$_2$NR$^{1b}$R$^{1c}$, —NR$^{1b}$R$^{1c}$, NR$^{1a}$C(O)R$^{1d}$—NR$^{1a}$C(O)OR$^{1d}$, —NR$^{1a}$C(O)NR$^{1b}$R$^{1c}$, —NR$^{1a}$C(O)SR$^{1d}$, —NR$^{1a}$C(=NR$^{1d}$)NR$^{1b}$R$^{1c}$, —NR$^{1a}$C(S)R$^{1d}$, —NR$^{1a}$C(S)OR$^{1d}$, —NR$^{1a}$C(S)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^4$ is $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl;

$R^6$ is $C_{5-10}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; and each $R^{1a}$, $R^{1b}$, $R^{1c}$, and $R^{1d}$ is independently hydrogen, deuterium, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more substituents $Q^a$; and (c) —C(O)$R^a$, —C(O)O$R^a$, —C(O)NR$^b$R$^c$, —C(O)SR$^a$, —C(NR$^a$)NR$^b$R$^c$, —C(S)R$^a$, —C(S)OR$^a$, —C(S)NR$^b$R$^c$, —OR$^a$, —OC(O)R$^a$, —OC(O)OR$^a$, —OC(O)NR$^b$R$^c$, —OC(O)SR$^a$, —OC(=NR$^a$)NR$^b$R$^c$, —OC(S)R$^a$, —OC(S)OR$^a$, —OC(S)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(O)SR$^d$, —NR$^a$C(=NR$^d$)NR$^b$R$^c$, —NR$^a$C(S)R$^d$, —NR$^a$C(S)OR$^d$, —NR$^a$C(S)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each $R^a$, $R^b$, $R^c$, and $R^d$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents $Q^a$; or (iii) $R^b$ and $R^c$ together with the N atom to which they are attached form heterocyclyl, optionally substituted with one or more substituents $Q^a$;

wherein each $Q^a$ is independently selected from: (a) deuterium, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(O)SR$^e$, —C(NR$^e$)NR$^f$R$^g$, —C(S)R$^e$, —C(S)OR$^e$, —C(S)NR$^f$R$^g$, —OR$^e$, —OC(O)R$^e$, —OC(O)OR$^e$, —OC(O)NR$^f$R$^g$, —OC(O)SR$^e$, —OC(=NR$^e$)NR$^f$R$^g$, —OC(S)R$^e$, —OC(S)OR$^e$, —OC(S)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(O)SR, —NR$^e$C(=NR$^h$)NR$^f$R$^g$, —NR$^e$C(S)R$^h$, —NR$^e$C(S)OR$^f$, —NR$^e$C(S)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each $R^e$, $R^f$, $R^g$, and $R^h$ is independently (i) hydrogen or deuterium; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

2. The pharmaceutical composition of claim 1, wherein $R^6$ is $C_{3-10}$ cycloalkyl, $C_{6-14}$ aryl, heteroaryl, or heterocyclolyl, each of which is optionally substituted with one or more substituents Q.

3. The pharmaceutical composition of claim 1, wherein $R^6$ is $C_{3-10}$ cycloalkyl, optionally substituted with one or more substituents Q.

4. The pharmaceutical composition of claim 1, wherein $R^6$ is cyclopropyl or cyclohexyl, each optionally substituted with one or more substituents Q.

5. The pharmaceutical composition of claim 1, wherein $R^6$ is $C_{6-14}$ aryl, optionally substituted with one or more substituents Q.

6. The pharmaceutical composition of claim 1, wherein $R^6$ is phenyl, optionally substituted with one or more substituents Q.

7. The pharmaceutical composition of claim 1, wherein $R^6$ is heteroaryl, optionally substituted with one or more substituents Q.

8. The pharmaceutical composition of claim 1, wherein $R^6$ is $C_{5-10}$ alkyl, optionally substituted with one or more substituents Q.

9. The pharmaceutical composition of claim 8, wherein $R^6$ is pentyl, optionally substituted with one or more substituents Q.

10. The pharmaceutical composition of claim 8, wherein $R^6$ is trimethylpentyl.

11. The pharmaceutical composition of claim 8, wherein $R^6$ is 2,4,4-trimethylpentyl.

12. The pharmaceutical composition of claim 1, wherein $R^4$ is $C_{1-6}$ alkyl, $C_{3-10}$ cycloalkyl, or $C_{6-14}$ aryl, each of which is optionally substituted with one or more substituents Q.

13. The pharmaceutical composition of claim 1, wherein $R^4$ is $C_{1-6}$ alkyl, optionally substituted with one or more substituents Q.

14. The pharmaceutical composition of claim 13, wherein $R^4$ is methyl, trifluoromethyl, or isopropyl.

15. The pharmaceutical composition of claim 1, wherein $R^4$ is $C_{6-14}$ aryl, optionally substituted with one or more substituents Q.

16. The pharmaceutical composition of claim 15, wherein $R^4$ is phenyl, optionally substituted with one or more substituents Q.

17. The pharmaceutical composition of claim 1, wherein $R^1$ is hydrogen.

18. The pharmaceutical composition of claim 1, wherein $R^3$ is hydrogen or deuterium.

19. The pharmaceutical composition of claim 1, wherein $R^5$ is hydrogen or deuterium.

20. The pharmaceutical composition of claim 1, wherein the compound is:
   6-cyclohexyl-4-methylpyridine-2(1H)-thione;
   6-cyclohexyl-4-trifluoromethylpyridine-2(1H)-thione;
   4-methyl-6-(2,4,4-trimethylpentyl)pyridine-2(1H)-thione;
   or
   6-cyclopropyl-4-methylpyridine-2(1H)-thione;
or an enantiomer, a mixture of enantiomers, a tautomer, a mixture of two or more tautomers, or an isotopic variant thereof; or a pharmaceutically acceptable salt, solvate, or hydrate thereof.

21. The pharmaceutical composition of claim 1, wherein the composition is in single dosage form.

22. The pharmaceutical composition of claim 1, wherein the composition is in an oral, parenteral, or intravenous dosage form.

23. The pharmaceutical composition of claim 22, wherein the oral dosage form is a tablet, capsule, or solution.

24. The pharmaceutical composition of claim 1, further comprising a second therapeutic agent.

25. A method for treating or ameliorating one or more symptoms of multiple sclerosis in a subject, comprising administering to the subject a pharmaceutical composition of claim 1.

26. The method of claim 25, wherein the multiple sclerosis is relapsing-remitting MS (RR-MS), primary progressive MS (PP-MS), progressive relapsing MS (PR-MS), or secondary progressive MS (SP-MS).

* * * * *